United States Patent
He et al.

(10) Patent No.: US 7,662,793 B2
(45) Date of Patent: Feb. 16, 2010

(54) INHIBITION OF HUMAN SQUAMOUS CELL CARCINOMA GROWTH IN VIVO BY EPIDERMAL GROWTH FACTOR RECEPTOR ANTISENSE RNA TRANSCRIBED FROM A POL III PROMOTER

(75) Inventors: Yukai He, Pittsburgh, PA (US); Jennifer R. Grandis, Pittsburgh, PA (US); Leaf Huang, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 722 days.

(21) Appl. No.: 10/387,252

(22) Filed: Mar. 12, 2003

(65) Prior Publication Data

US 2004/0047847 A1    Mar. 11, 2004

Related U.S. Application Data

(62) Division of application No. 09/595,863, filed on Jun. 16, 2000, now abandoned.

(60) Provisional application No. 60/140,136, filed on Jun. 18, 1999.

(51) Int. Cl.
C07H 21/02 (2006.01)
C07H 21/04 (2006.01)
A61K 31/70 (2006.01)
A01N 43/04 (2006.01)

(52) U.S. Cl. .................. 514/44; 536/23.1; 536/24.3; 536/24.33; 536/24.5

(58) Field of Classification Search ............... 536/23.1, 536/24.3, 24.33, 24.5; 435/6, 91.1, 325, 435/375; 514/44
See application file for complete search history.

(56) References Cited

U.S. PATENT DOCUMENTS 5,610,288 A * 3/1997 Rubenstein ............... 536/24.5

OTHER PUBLICATIONS

He et al. Inhibition of Human Squamous Cell Carcinoma Growth In vivo by Epidermal Growth Factor Receptor Antisense RNA Transcribed From the U6 Promoter. Journal of Natl. Cancer Inst., 1998 vol. 90:1080-1087.*
He et al. Growth Inhibiton of Human Papillomavirus 16 DNA-positive mouse tumor by antisense RNA transcribed from U6 Promoter. Cancer Research, 1997 vol. 57:3993-3999.*
Good et al. (Gene Therapeutics, 1997 vol. 4:45-54).*

* cited by examiner

*Primary Examiner*—Sean McGarry
*Assistant Examiner*—Terra Cotta Gibbs
(74) *Attorney, Agent, or Firm*—Barbara E. Johnson, Esq.

(57) ABSTRACT

A nucleic acid is provided comprising an expression cassette which includes transcription control sequences of a member of a class of Pol III-transcribed genes in which no transcribed portion of the Pol III gene is required for transcription of the gene. In the expression cassette, the transcribed 5' hairpin structure of the Pol III gene is deleted. The transcription control sequences are operably linked to a sequence of an EGFR gene in an antisense orientation suitable for decreasing expression of EGFR in the cell when transcribed. Lastly, a method for decreasing expression of EGFR in cells is provided that includes the step of contacting target cells either parenterally or directly into the tumor or tissue adjacent to the tumor cells with the nucleic acid of the present invention.

10 Claims, 18 Drawing Sheets

FIG. 5A
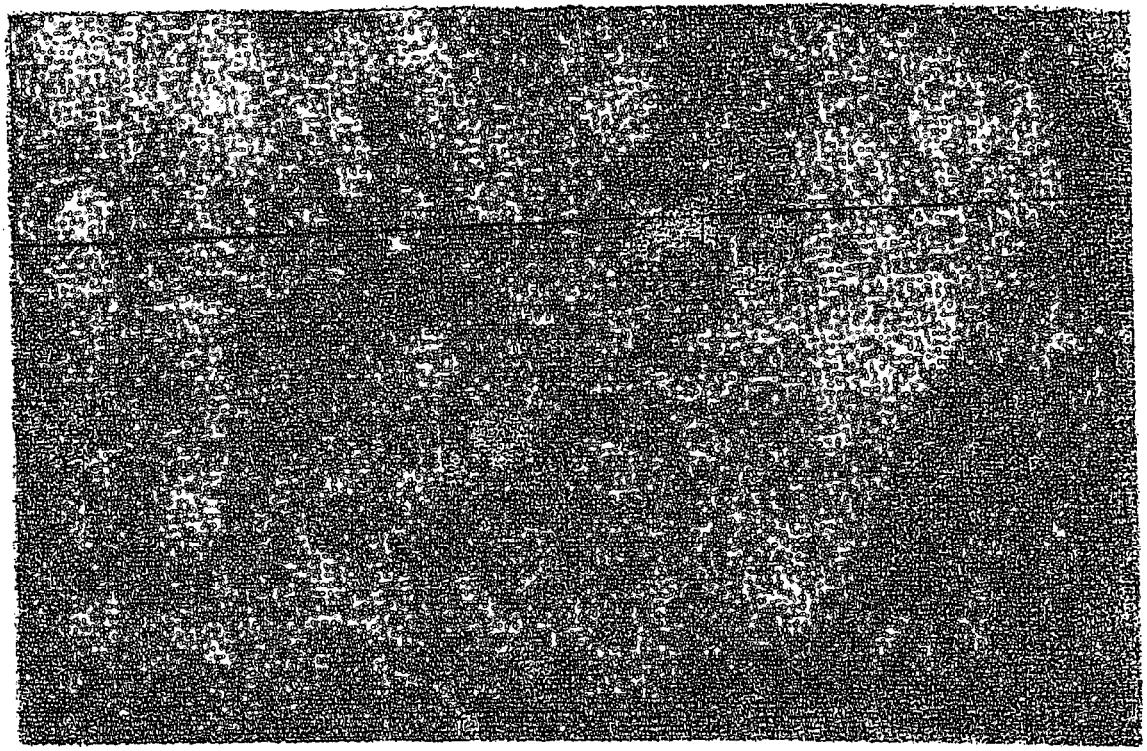
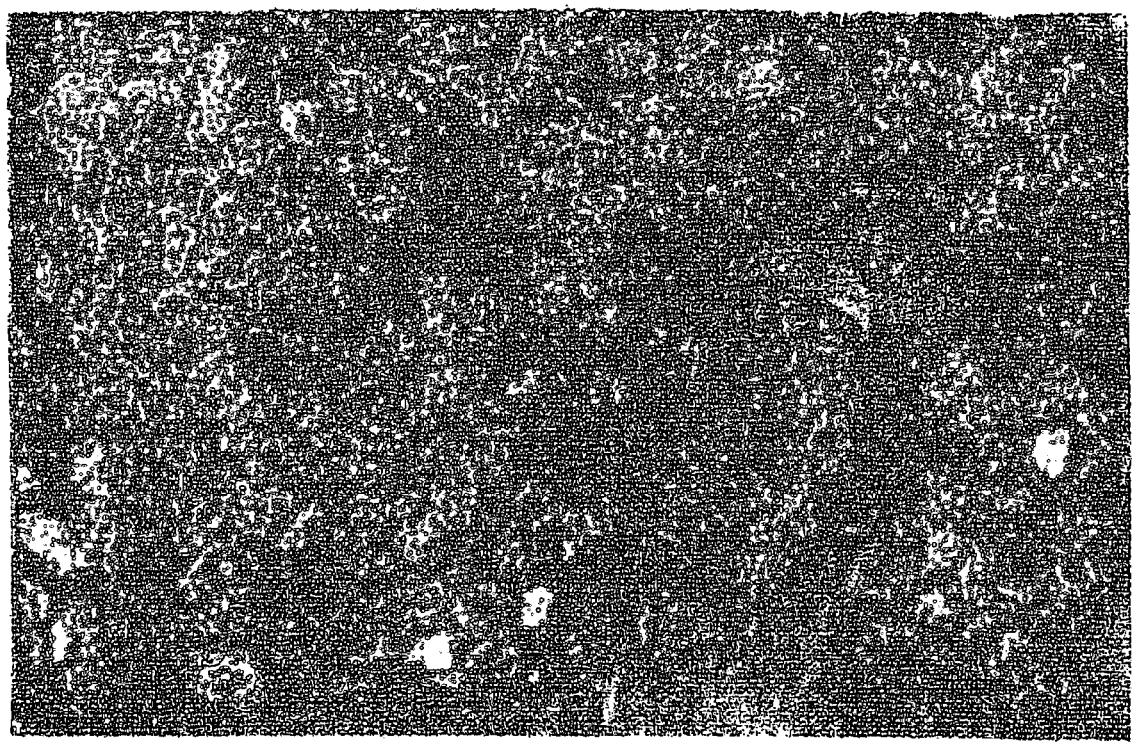
FIG. 5B

FIG. 8A
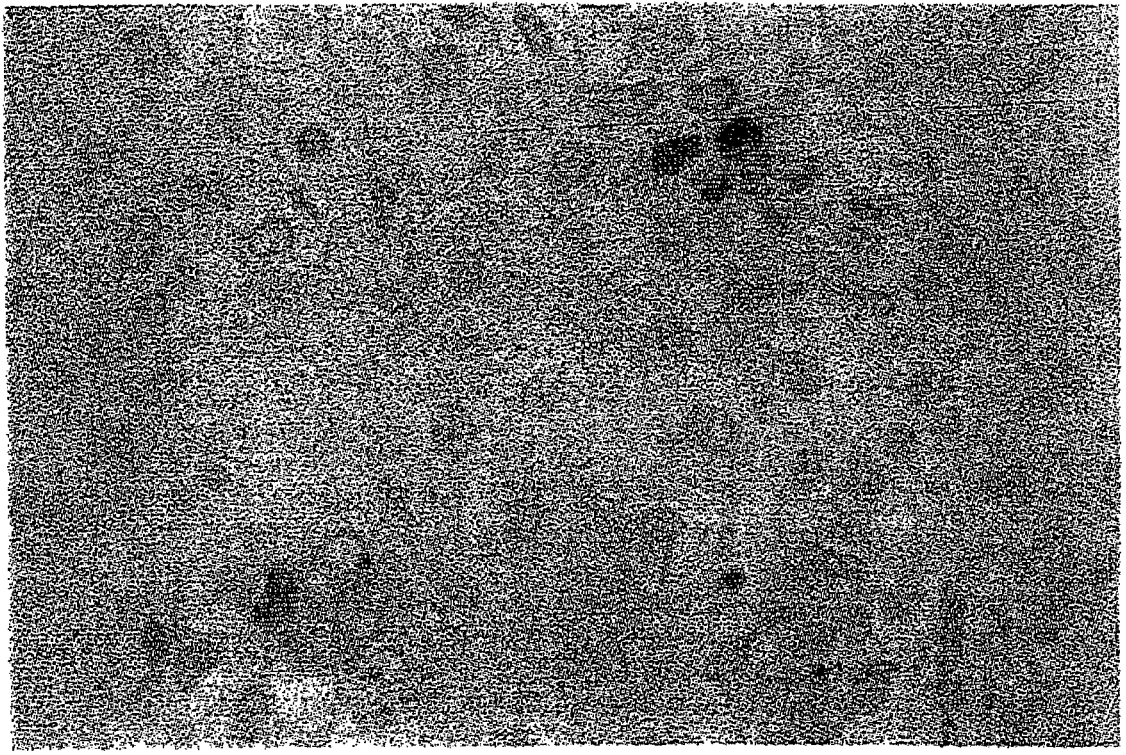
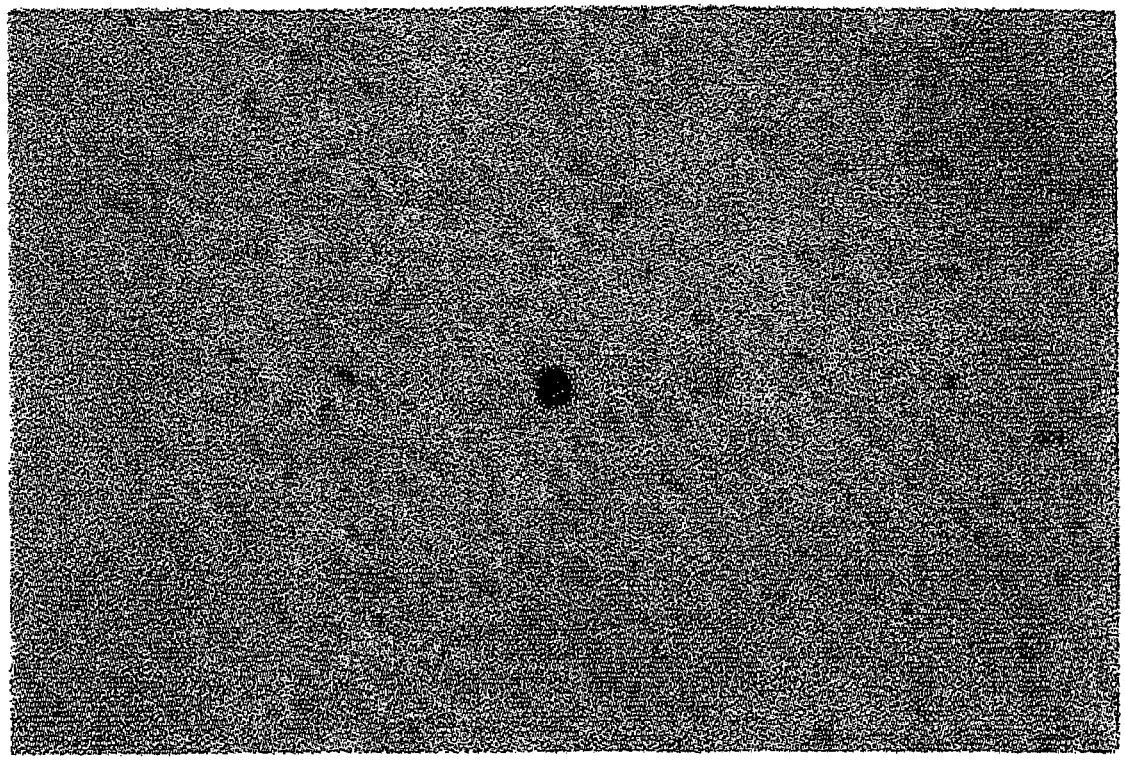
FIG. 8B

```
GCCGCGCTGC GCCGGAGTCC CGAGCTAGCC CCGGCGCCGC CGCCGCCCAG ACCGGACGAC  61
AGGCCACCTC GTCGGCGTCC GCCCGAGTCC CCGCCTCGCC GCCAACGCCA CAACCACCGC 121
GCACGGCCCC CTGACTCCGT CCAGTATTGA TCGGGAGAGC CGGAGCGAGC TCTTCGGGGA 181
GCAGCGATGC GACCCTCCGG GACGGCCGGG GCAGCGCTCC TGGCGCTGCT GGCTGCGCTC 241
TGCCCGGCGA GTCGGCTCT  GGAGGAAAAG AAAGTTTGCC AAGGCACGAG TAACAAGCTC 301
ACGCAGTTGG GCACTTTTGA AGATCATTTT CTCAGCCTCC AGAGGATGTT CAATAACTGT 361
GAGGTGGTCC TTGGGAATTT GGAAATTACC TATGTGCAGA GGAATTATGA TCTTTCCTTC 421
TTAAAGACCA TCCAGGAGGT GGCTGGTTAT GTCCTCATTG CCCTCAACAC AGTGGAGCGA 481
ATTCCTTTGG AAAACCTGCA GATCATCAGA GGAAATATGT ACTACGAAAA TTCCTATGCC 541
TTAGCAGTCT TATCTAACTA TGATGCAAAT AAAACCGGAC TGAAGGAGCT GCCCATGAGA 601
AATTTACAGG AAATCCTGCA TGGCGCCGTG CGGTTCAGCA ACAACCCTGC CCTGTGCAAC 661
GTGGAGAGCA TCCAGTGGCG GGACATAGTC AGCAGTGACT TTCTCAGCAA CATGTCGATG 721
GACTTCCAGA ACCACCTGGG CAGCTGCCAA AAGTGTGATC CAAGCTGTCC CAATGGGAGC 781
TGCTGGGGTG CAGGAGAGGA GAACTGCCAG AAACTGACCA AAATCATCTG TGCCCAGCAG 841
TGCTCCGGGC GCTGCCGTGG CAAGTCCCCC AGTGACTGCT GCCACAACCA GTGTGCTGCA 901
GGCTGCACAG GCCCCCGGGA GAGCGACTGC CTGGTCTGCC GCAAATTCCG AGACGAAGCC 961
ACGTGCAAGG ACACCTGCCC CCCACTCATG CTCTACAACC CCACCACGTA CCAGATGGAT 1021
GTGAACCCCG AGGGCAAATA CAGCTTTGGT GCCACCTGCG TGAAGAAGTG TCCCCGTAAT 1081
TATGTGGTGA CAGATACGG  CTCGTGCGTC CGAGCCTGTG GGCCGACAG  CTATGAGATG 1141
GAGGAAGACG GCGTCCGCAA GTGTAAGAAG TGCGAAGGGC CTTGCCGCAA AGTGTGTAAC 1201
GGAATAGGTA TTGGTGAATT TAAAGACTCA CTCTCCATAA ATGCTACGAA TATTAAACAC 1261
TTCAAAAACT GCACCTCCAT CAGTGGCGAT CTCCACATCC TGCCGGTGGC ATTTAGGGGT 1321
GACTCCTTCA CACATACTCC TCCTCTGGAT CCACAGGAAC TGGATATTCT GAAAACCGTA 1381
AAGGAAATCA CAGGGTTTTT GCTGATTCAG GCTTGGCCTG AAAACAGGAC GGACCTCCAT 1441
GCCTTTGAGA ACCTAGAAAT CATACGCGGC AGGACCAAGC AACATGGTCA GTTTTCTCTT 1501
GCAGTCGTCA GCCTGAACAT AACATCCTTG GGATTACGCT CCCTCAAGGA GATAAGTGAT 1561
GGAGATGTGA TAATTTCAGG AAACAAAAAT TTGTGCTATG CAAATACAAT AAACTGGAAA 1621
AAACTGTTTG GGACCTCCGG TCAGAAAACC AAAATTATAA GCAACAGAGG TGAAAACAGC 1681
TGCAAGGCCA CAGGCCAGGT CTGCCATGCC TTGTGCTCCC CCGAGGGCTG CTGGGGCCCG 1741
GAGCCCAGGG ACTGCGTCTC TTGCCGGAAT GTCAGCCGAG GCAGGGAATG CGTGGACAAG 1801
TGCAAGCTTC TGGAGGGTGA GCCAAGGGAG TTTGTGGAGA ACTCTGAGTG CATACAGTGC 1861
CACCCAGAGT GCCTGCCTCA GGCCATGAAC ATCACCTGCA CAGGACGGGG ACCAGACAAC 1921
TGTATCCAGT GTGCCCACTA CATTGACGGC CCCCACTGCG TCAAGACCTG CCCGGCAGGA 1981
GTCATGGGAG AAAACAACAC CCTGGTCTGG AAGTACGCAG ACGCCGGCCA TGTGTGCCAC 2041
CTGTGCCATC CAAACTGCAC CTACGGATGC ACTGGGCCAG GTCTTGAAGG CTGTCCAACG 2101
AATGGGCCTA AGATCCCGTC CATCGCCACT GGGATGGTGG GGGCCCTCCT CTTGCTGCTG 2161
GTGGTGGCCC TGGGGATCGG CCTCTTCATG CGAAGGCGCC ACATCGTTCG GAAGCGCACG 2221
CTGCGGAGGC TGCTGCAGGA GAGGGAGCTT GTGGAGCCTC TTACACCCAG TGGAGAAGCT 2281
CCCAACCAAG CTCTCTTGAG GATCTTGAAG GAAACTGAAT TCAAAAAGAT CAAAGTGCTG 2341
GGCTCCGGTG CGTTCGGCAC GGTGTATAAG GGACTCTGGA TCCCAGAAGG TGAGAAAGTT 2401
AAAATTCCCG TCGCTATCAA GGAATTAAGA GAAGCAACAT CTCCGAAAGC CAACAAGGAA 2461
ATCCTCGATG AAGCCTACGT GATGGCCAGC GTGGACAACC CCCACGTGTG CCGCCTGCTG 2521
GGCATCTGCC TCACCTCCAC CGTGCAACTC ATCACGCAGC TCATGCCCTT CGGCTGCCTC 2581
```

Fig. 9/1

```
CTGGACTATG TCCGGGAACA CAAAGACAAT ATTGGCTCCC AGTACCTGCT CAACTGGTGT 2641
GTGCAGATCG CAAAGGGCAT GAACTACTTG GAGGACCGTC GCTTGGTGCA CCGCGACCTG 2701
GCAGCCAGGA ACGTACTGGT GAAAACACCG CAGCATGTCA AGATCACAGA TTTTGGGCTG 2761
GCCAAACTGC TGGGTGCGGA AGAGAAAGAA TACCATGCAG AAGGAGGCAA AGTGCCTATC 2821
AAGTGGATGG CATTGGAATC AATTTTACAC AGAATCTATA CCCACCAGAG TGATGTCTGG 2881
AGCTACGGGG TGACCGTTTG GGAGTTGATG ACCTTTGGAT CCAAGCCATA TGACGGAATC 2941
CCTGCCAGCG AGATCTCCTC CATCCTGGAG AAAGGAGAAC GCCTCCCTCA GCCACCCATA 3001
TGTACCATCG ATGTCTACAT GATCATGGTC AAGTGCTGGA TGATAGACGC AGATAGTCGC 3061
CCAAAGTTCC GTGAGTTGAT CATCGAATTC TCCAAAATGG CCCGAGACCC CCAGCGCTAC 3121
CTTGTCATTC AGGGGGATGA AAGAATGCAT TTGCCAAGTC CTACAGACTC AACTTCTAC 3181
CGTGCCCTGA TGGATGAAGA AGACATGGAC GACGTGGTGG ATGCCGACGA GTACCTCATC 3241
CCACAGCAGG GCTTCTTCAG CAGCCCCTCC ACGTACGGA CTCCCCTCCT GAGCTCTCTG 3301
AGTGCAACCA GCAACAATTC CACCGTGGCT TGCATTGATA GAAATGGGCT GCAAAGCTGT 3361
CCCATCAAGG AAGACAGCTT CTTGCAGCGA TACAGCTCAG ACCCCACAGG CGCCTTGACT 3421
GAGGACAGCA TAGACGACAC CTTCCTCCCA GTGCCTGAAT ACATAAACCA GTCCGTTCCC 3481
AAAAGGCCCG CTGGCTCTGT GCAGAATCCT GTCTATCACA ATCAGCCTCT GAACCCCGCG 3541
CCCAGCAGAG ACCCACACTA CCAGGACCCC CACAGCACTG CAGTGGGCAA CCCCGAGTAT 3601
CTCAACACTG TCCAGCCCAC CTGTGTCAAC AGCACATTCG ACAGCCCTGC CCACTGGGCC 3661
CAGAAAGGCA GCCACCAAAT TAGCCTGGAC AACCCTGACT ACCAGCAGGA CTTCTTTCCC 3721
AAGGAAGCCA AGCCAAATGG CATCTTTAAG GGCTCCACAG CTGAAAATGC AGAATACCTA 3781
AGGGTCGCGC CACAAAGCAG TGAATTTATT GGAGCATGAC CACGGAGGAT AGTATGAGCC 3841
CTAAAAATCC AGACTCTTTC GATACCCAGG ACCAAGCCAC AGCAGGTCCT CCATCCCAAC 3901
AGCCATGCCC GCATTAGCTC TTAGACCCAC AGACTGGTTT TGCAACGTTT ACACCGACTA 3961
GCCAGGAAGT ACTTCCACCT CGGGCACATT TTGGGAAGTT GCATTCCTTT GTCTTCAAAC 4021
TGTGAAGCAT TTACAGAAAC GCATCCAGCA AGAATATTGT CCCTTTGAGC AGAAATTTAT 4081
CTTTCAAAGA GGTATATTTG AAAAAAAAAA AAAAAGTATA TGTGAGGATT TTTATTGATT 4141
GGGGATCTTG GAGTTTTTCA TTGTCGCTAT TGATTTTTAC TTCAATGGGC TCTTCCAACA 4201
AGGAAGAAGC TTGCTGGTAG CACTTGCTAC CCTGAGTTCA TCCAGGCCCA ACTGTGAGCA 4261
AGGAGCACAA GCCACAAGTC TTCCAGAGGA TGCTTGATTC CAGTGGTTCT GCTTCAAGGC 4321
TTCCACTGCA AAACACTAAA GATCCAAGAA GGCCTTCATG GCCCCAGCAG GCCGGATCGG 4381
TACTGTATCA AGTCATGGCA GGTACAGTAG GATAAGCCAC TCTGTCCCTT CCTGGGCAAA 4441
GAAGAAACGG AGGGGATGAA TTCTTCCTTA GACTTACTTT TGTAAAAATG TCCCCACGGT 4501
ACTTACTCCC CACTGATGGA CCAGTGGTTT CCAGTCATGA GCGTTAGACT GACTTGTTTG 4561
TCTTCCATTC CATTGTTTTG AAACTCAGTA TGCCGCCCCT GTCTTGCTGT CATGAAATCA 4621
GCAAGAGAGG ATGACACATC AAATAATAAC TCGGATTCCA GCCCACATTG GATTCATCAG 4681
CATTTGGACC AATAGCCCAC AGCTGAGAAT GTGGAATACC TAAGGATAAC ACCGCTTTTG 4741
TTCTCGCAAA AACGTATCTC CTAATTTGAG GCTCAGATGA AATGCATCAG GTCCTTTGGG 4801
GCATAGATCA GAAGACTACA AAAATGAAGC TGCTCTGAAA TCTCCTTTAG CCATCACCCC 4861
AACCCCCCAA AATTAGTTTG TGTTACTTAT GGAAGATAGT TTTCTCCTTT TACTTCACTT 4921
CAAAAGCTTT TTACTCAAAG AGTATATGTT CCCTCCAGGT CAGCTGCCCC CAAACCCCCT 4981
CCTTACGCTT TGTCACACAA AAAGTGTCTC TGCCTTGAGT CATCTATTCA AGCACTTACA 5041
GCTCTGGCCA CAACAGGGCA TTTTACAGGT GCGAATGACA GTAGCATTAT GAGTAGTGTG 5101
AATTCAGGTA GTAAATATGA AACTAGGGTT TGAAATTGAT AATGCTTTCA CAACATTTGC 5161
```

Fig. 9/2

```
AGATGTTTTA GAAGGAAAAA AGTTCCTTCC TAAAATAATT TCTCTACAAT TGGAAGATTG 5221
GAAGATTCAG CTAGTTAGGA GCCCATTTTT TCCTAATCTG TGTGTGCCCT GTAACCTGAC 5281
TGGTTAACAG CAGTCCTTTG TAAACAGTGT TTTAAACTCT CCTAGTCAAT ATCCACCCCA 5341
TCCAATTTAT CAAGGAAGAA ATGGTTCAGA AAATATTTTC AGCCTACAGT TATGTTCAGT 5401
CACACACACA TACAAAATGT TCCTTTTGCT TTTAAAGTAA TTTTTGACTC CCAGATCAGT 5461
CAGAGCCCCT ACAGCATTGT TAAGAAAGTA TTTGATTTTT GTCTCAATGA AAATAAAACT 5521
ATATTCATTT CC
```

Fig. 9/3

```
tggccattgc atacgttgta tccatatcat aatatgtaca tttatattgg ctcatgtcca   61
acattaccgc catgttgaca ttgattattg actagttatt aatagtaatc aattacgggg  121
tcattagttc atagcccata tatggagttc cgcgttacat aacttacggt aaatggcccg  181
cctggctgac cgcccaacga cccccgccca ttgacgtcaa taatgacgta tgttcccata  241
gtaacgccaa tagggacttt ccattgacgt caatgggtgg agtatttacg gtaaactgcc  301
cacttggcag tacatcaagt gtatcatatg ccaagtacgc ccctattga cgtcaatgac  361
ggtaaatggc ccgcctggca ttatgcccag tacatgacct tatgggactt tcctacttgg  421
cagtacatct acgtattagt catcgctatt accatggtga tgcggttttg gcagtacatc  481
aatgggcgtg gatagcggtt tgactcacgg ggatttccaa gtctccaccc cattgacgtc  541
aatgggagtt tgttttggca ccaaaatcaa cgggactttc caaaatgtcg taacaactcc  601
gccccattga cgcaaatggg cggtaggcgt gtacggtggg aggtctatat aagcagagct  661
cgtttagtga accgtcagat cgcctggaga cgccatccac gctgttttga cctccataga  721
agacaccggg accgatccag cctccgcggc cgggaacggt gcattggaac gcggattccc  781
cgtgccaaga gtgacgtaag taccgcctat agagtctata ggcccacccc cttggcttct  841
tatgcatgct atactgtttt tggcttgggg tctatacacc cccgcttcct catgttatag  901
gtgatggtat agcttagcct ataggtgtgg gttattgacc attattgacc actccaacgg  961
tggagggcag tgtagtctga gcagtactcg ttgctgccgc gcgcgccacc agacataata 1021
gctgacagac taacagactg ttccttttcca tgggtctttt ctgcagtcac cgtcgtcgac 1081
ggtatcgata agcttgatat cagatctttt tccctctgcc aaaaattatg gggacatcat 1141
gaagccccttt gagcatctga cttctggcta ataaaggaaa tttatttcat tgcaatagtg 1201
tgttggaatt ttttgtgtct ctcactcgga aggacatatg ggagggcaaa tcatttaaaa 1261
catcagaatc agtatttggt ttagagtttg gcaacatatg ccattcttcc gcttcctcgc 1321
tcactgactc gctgcgctcg gtcgttcggc tgcggcgagc ggtatcagct cactcaaagg 1381
cggtaatacg gttatccaca gaatcagggg ataacgcagg aagaacatg tgagcaaaag 1441
gccagcaaaa ggccaggaac cgtaaaaagg ccgcgttgct ggcgttttc cataggctcc 1501
gccccccctga cgagcatcac aaaaatcgac gctcaagtca gaggtggcga acccgacag 1561
gactataaag ataccaggcg tttccccctg gaagctccct cgtgcgctct cctgttccga 1621
ccctgccgct taccggatac ctgtccgcct ttctcccttc gggaagcgtg gcgctttctc 1681
aatgctcacg ctgtaggtat ctcagttcgg tgtaggtcgt tcgctccaag ctgggctgtg 1741
tgcacgaacc ccccgttcag·cccgaccgct gcgccttatc cggtaactat cgtcttgagt 1801
ccaacccggt aagacacgac ttatcgccac tggcagcagc cactggtaac aggattagca 1861
gagcgaggta tgtaggcggt gctacagagt tcttgaagtg gtggcctaac tacggctaca 1921
ctagaaggac agtatttggt atctgcgctc tgctgaagcc agttaccttc ggaaaaagag 1981
ttggtagctc ttgatccggc aaacaaacca ccgctggtag cggtggtttt tttgtttgca 2041
agcagcagat tacgcgcaga aaaaaggat ctcaagaaga tccttgatc ttttctacgg 2101
ggtctgacgc tcagtggaac gaaaactcac gttaagggat tttggtcatg agattatcaa 2161
aaaggatctt cacctagatc cttttaaatt aaaaatgaag ttttaaatca atctaaagta 2221
tatatgagta aacttggtct gacagttacc aatgcttaat cagtgaggca cctatctcag 2281
cgatctgtct atttcgttca tccatagttg cctgactcgg ggggggggg cgctgaggtc 2341
tgcctcgtga agaaggtgtt gctgactcat accaggcctg aatcgcccca tcatccagcc 2401
agaaagtgag ggagccacgg ttgatgagag ctttgttgta ggtggaccag ttggtgattt 2461
tgaactttg ctttgccacg aacggtctg cgttgtcggg aagatgcgtg atctgatcct 2521
tcaactcagc aaaagttcga tttattcaac aaagccgccg tcccgtcaag tcagcgtaat 2581
gctctgccag tgttacaacc aattaaccaa ttctgattag aaaaactcat cgagcatcaa 2641
```

Fig. 10/1

```
atgaaactgc aatttattca tatcaggatt atcaatacca tattttgaa  aaagccgttt 2701
ctgtaatgaa ggagaaaact caccgaggca gttccatagg atggcaagat cctggtatcg 2761
gtctgcgatt ccgactcgtc caacatcaat acaacctatt aatttcccct cgtcaaaaat 2821
aaggttatca agtgagaaat caccatgagt gacgactgaa tccggtgaga atggcaaaag 2881
cttatgcatt tctttccaga cttgttcaac aggccagcca ttacgctcgt catcaaaatc 2941
actcgcatca accaaaccgt tattcattcg tgattgcgcc tgagcgagac gaaatacgcg 3001
atcgctgtta aaaggacaat tacaaacagg aatcgaatgc aaccggcgca ggaacactgc 3061
cagcgcatca acaatatttt cacctgaatc aggatattct tctaatacct ggaatgctgt 3121
tttcccgggg atcgcagtgg tgagtaacca tgcatcatca ggagtacgga taaatgctt  3181
gatggtcgga agaggcataa attccgtcag ccagtttagt ctgaccatct catctgtaac 3241
atcattggca acgctacctt tgccatgttt cagaaacaac tctggcgcat cgggcttccc 3301
atacaatcga tagattgtcg cacctgattg cccgacatta tcgcgagccc atttatacc  3361
atataaatca gcatccatgt tggaatttaa tcgcggcctc gagcaagacg tttcccgttg 3421
aatatggctc ataacacccc ttgtattact gtttatgtaa gcagacagtt ttattgttca 3481
tgatgatata tttttatctt gtgcaatgta acatcagaga ttttgagaca caacgtggct 3541
ttccccccc  cccattatt  gaagcattta tcagggttat tgtctcatga gcggatacat 3601
atttgaatgt atttagaaaa ataaacaaat aggggttccg cgcacatttc ccgaaaagt  3661
gccacctgac gtctaagaaa ccattattat catgacatta acctataaaa ataggcgtat 3721
cacgaggccc tttcgtcctc gcgcgtttcg gtgatgacgg tgaaaacctc tgacacatgc 3781
agctcccgga gacggtcaca gcttgtctgt aagcggatgc cgggagcaga caagcccgtc 3841
agggcgcgtc agcgggtgtt ggcgggtgtc ggggctggct taactatgcg gcatcagagc 3901
agattgtact gagagtgcac catatgcggt gtgaaatacc gcacagatgc gtaaggagaa 3961
aataccgcat cagattggct at
```

Fig. 10/2

SEQUENCE LISTING

```
<160> NUMBER OF SEQ ID NOS: 5

<210> SEQ ID NO 1
<211> LENGTH: 5532
<212> TYPE: DNA
<213> ORGANISM: Homo sapiens
<220> FEATURE:
<221> NAME/KEY: CDS
<222> LOCATION: (187)..(3819)

<400> SEQUENCE: 1
gccgcgctgc gccggagtcc cgagctagcc ccggcgccgc cgccgcccag accggacgac      60
aggccacctc gtcggcgtcc gcccgagtcc ccgcctcgcc gccaacgcca caaccaccgc     120
gcacggcccc ctgactccgt ccagtattga tcgggagagc cggagcgagc tcttcgggga     180 gcagcg atg cga ccc tcc ggg acg gcc ggg gca gcg ctc ctg gcg ctg       228
       Met Arg Pro Ser Gly Thr Ala Gly Ala Ala Leu Leu Ala Leu
         1               5                  10 ctg gct gcg ctc tgc ccg gcg agt cgg gct ctg gag gaa aag aaa gtt       276
Leu Ala Ala Leu Cys Pro Ala Ser Arg Ala Leu Glu Glu Lys Lys Val
 15                  20                  25                  30 tgc caa ggc acg agt aac aag ctc acg cag ttg ggc act ttt gaa gat       324
Cys Gln Gly Thr Ser Asn Lys Leu Thr Gln Leu Gly Thr Phe Glu Asp
                 35                  40                  45
```

```
cat ttt ctc agc ctc cag agg atg ttc aat aac tgt gag gtg gtc ctt      372
His Phe Leu Ser Leu Gln Arg Met Phe Asn Asn Cys Glu Val Val Leu
             50                  55                  60 ggg aat ttg gaa att acc tat gtg cag agg aat tat gat ctt tcc ttc      420
Gly Asn Leu Glu Ile Thr Tyr Val Gln Arg Asn Tyr Asp Leu Ser Phe
         65                  70                  75 tta aag acc atc cag gag gtg gct ggt tat gtc ctc att gcc ctc aac      468
Leu Lys Thr Ile Gln Glu Val Ala Gly Tyr Val Leu Ile Ala Leu Asn
     80                  85                  90 aca gtg gag cga att cct ttg gaa aac ctg cag atc atc aga gga aat      516
Thr Val Glu Arg Ile Pro Leu Glu Asn Leu Gln Ile Ile Arg Gly Asn
 95                 100                 105                 110 atg tac tac gaa aat tcc tat gcc tta gca gtc tta tct aac tat gat      564
Met Tyr Tyr Glu Asn Ser Tyr Ala Leu Ala Val Leu Ser Asn Tyr Asp
                115                 120                 125 gca aat aaa acc gga ctg aag gag ctg ccc atg aga aat tta cag gaa      612
Ala Asn Lys Thr Gly Leu Lys Glu Leu Pro Met Arg Asn Leu Gln Glu
            130                 135                 140 atc ctg cat ggc gcc gtg cgg ttc agc aac aac cct gcc ctg tgc aac      660
Ile Leu His Gly Ala Val Arg Phe Ser Asn Asn Pro Ala Leu Cys Asn
        145                 150                 155 gtg gag agc atc cag tgg cgg gac ata gtc agc agt gac ttt ctc agc      708
Val Glu Ser Ile Gln Trp Arg Asp Ile Val Ser Ser Asp Phe Leu Ser
160                 165                 170 aac atg tcg atg gac ttc cag aac cac ctg ggc agc tgc caa aag tgt      756
Asn Met Ser Met Asp Phe Gln Asn His Leu Gly Ser Cys Gln Lys Cys
175                 180                 185                 190 gat cca agc tgt ccc aat ggg agc tgc tgg ggt gca gga gag gag aac      804
Asp Pro Ser Cys Pro Asn Gly Ser Cys Trp Gly Ala Gly Glu Glu Asn
                195                 200                 205 tgc cag aaa ctg acc aaa atc atc tgt gcc cag cag tgc tcc ggg cgc      852
Cys Gln Lys Leu Thr Lys Ile Ile Cys Ala Gln Gln Cys Ser Gly Arg
            210                 215                 220 tgc cgt ggc aag tcc ccc agt gac tgc tgc cac aac cag tgt gct gca      900
Cys Arg Gly Lys Ser Pro Ser Asp Cys Cys His Asn Gln Cys Ala Ala
        225                 230                 235 ggc tgc aca ggc ccc cgg gag agc gac tgc ctg gtc tgc cgc aaa ttc      948
Gly Cys Thr Gly Pro Arg Glu Ser Asp Cys Leu Val Cys Arg Lys Phe
    240                 245                 250 cga gac gaa gcc acg tgc aag gac acc tgc ccc cca ctc atg ctc tac      996
Arg Asp Glu Ala Thr Cys Lys Asp Thr Cys Pro Pro Leu Met Leu Tyr
255                 260                 265                 270 aac ccc acc acg tac cag atg gat gtg aac ccc gag ggc aaa tac agc     1044
Asn Pro Thr Thr Tyr Gln Met Asp Val Asn Pro Glu Gly Lys Tyr Ser
                275                 280                 285 ttt ggt gcc acc tgc gtg aag aag tgt ccc cgt aat tat gtg gtg aca     1092
Phe Gly Ala Thr Cys Val Lys Lys Cys Pro Arg Asn Tyr Val Val Thr
            290                 295                 300 gat cac ggc tcg tgc gtc cga gcc tgt ggg gcc gac agc tat gag atg     1140
Asp His Gly Ser Cys Val Arg Ala Cys Gly Ala Asp Ser Tyr Glu Met
        305                 310                 315 gag gaa gac ggc gtc cgc aag tgt aag aag tgc gaa ggg cct tgc cgc     1188
Glu Glu Asp Gly Val Arg Lys Cys Lys Lys Cys Glu Gly Pro Cys Arg
    320                 325                 330 aaa gtg tgt aac gga ata ggt att ggt gaa ttt aaa gac tca ctc tcc     1236
Lys Val Cys Asn Gly Ile Gly Ile Gly Glu Phe Lys Asp Ser Leu Ser
335                 340                 345                 350 ata aat gct acg aat att aaa cac ttc aaa aac tgc acc tcc atc agt     1284
Ile Asn Ala Thr Asn Ile Lys His Phe Lys Asn Cys Thr Ser Ile Ser
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 355 |     |     |     |     | 360 |     |     |     |     | 365 |     |     |      |
| ggc | gat | ctc | cac | atc | ctg | ccg | gtg | gca | ttt | agg | ggt | gac | tcc | ttc | aca | 1332 |
| Gly | Asp | Leu | His | Ile | Leu | Pro | Val | Ala | Phe | Arg | Gly | Asp | Ser | Phe | Thr |      |
|     |     |     | 370 |     |     |     |     | 375 |     |     |     |     | 380 |     |     |      |
| cat | act | cct | cct | ctg | gat | cca | cag | gaa | ctg | gat | att | ctg | aaa | acc | gta | 1380 |
| His | Thr | Pro | Pro | Leu | Asp | Pro | Gln | Glu | Leu | Asp | Ile | Leu | Lys | Thr | Val |      |
|     |     | 385 |     |     |     |     | 390 |     |     |     |     | 395 |     |     |     |      |
| aag | gaa | atc | aca | ggg | ttt | ttg | ctg | att | cag | gct | tgg | cct | gaa | aac | agg | 1428 |
| Lys | Glu | Ile | Thr | Gly | Phe | Leu | Leu | Ile | Gln | Ala | Trp | Pro | Glu | Asn | Arg |      |
|     | 400 |     |     |     |     | 405 |     |     |     |     | 410 |     |     |     |     |      |
| acg | gac | ctc | cat | gcc | ttt | gag | aac | cta | gaa | atc | ata | cgc | ggc | agg | acc | 1476 |
| Thr | Asp | Leu | His | Ala | Phe | Glu | Asn | Leu | Glu | Ile | Ile | Arg | Gly | Arg | Thr |      |
| 415 |     |     |     |     | 420 |     |     |     |     | 425 |     |     |     |     | 430 |      |
| aag | caa | cat | ggt | cag | ttt | tct | ctt | gca | gtc | gtc | agc | ctg | aac | ata | aca | 1524 |
| Lys | Gln | His | Gly | Gln | Phe | Ser | Leu | Ala | Val | Val | Ser | Leu | Asn | Ile | Thr |      |
|     |     |     |     | 435 |     |     |     |     | 440 |     |     |     |     | 445 |     |      |
| tcc | ttg | gga | tta | cgc | tcc | ctc | aag | gag | ata | agt | gat | gga | gat | gtg | ata | 1572 |
| Ser | Leu | Gly | Leu | Arg | Ser | Leu | Lys | Glu | Ile | Ser | Asp | Gly | Asp | Val | Ile |      |
|     |     |     | 450 |     |     |     |     | 455 |     |     |     |     | 460 |     |     |      |
| att | tca | gga | aac | aaa | aat | ttg | tgc | tat | gca | aat | aca | ata | aac | tgg | aaa | 1620 |
| Ile | Ser | Gly | Asn | Lys | Asn | Leu | Cys | Tyr | Ala | Asn | Thr | Ile | Asn | Trp | Lys |      |
|     |     | 465 |     |     |     |     | 470 |     |     |     |     | 475 |     |     |     |      |
| aaa | ctg | ttt | ggg | acc | tcc | ggt | cag | aaa | acc | aaa | att | ata | agc | aac | aga | 1668 |
| Lys | Leu | Phe | Gly | Thr | Ser | Gly | Gln | Lys | Thr | Lys | Ile | Ile | Ser | Asn | Arg |      |
|     | 480 |     |     |     |     | 485 |     |     |     |     | 490 |     |     |     |     |      |
| ggt | gaa | aac | agc | tgc | aag | gcc | aca | ggc | cag | gtc | tgc | cat | gcc | ttg | tgc | 1716 |
| Gly | Glu | Asn | Ser | Cys | Lys | Ala | Thr | Gly | Gln | Val | Cys | His | Ala | Leu | Cys |      |
| 495 |     |     |     |     | 500 |     |     |     |     | 505 |     |     |     |     | 510 |      |
| tcc | ccc | gag | ggc | tgc | tgg | ggc | ccg | gag | ccc | agg | gac | tgc | gtc | tct | tgc | 1764 |
| Ser | Pro | Glu | Gly | Cys | Trp | Gly | Pro | Glu | Pro | Arg | Asp | Cys | Val | Ser | Cys |      |
|     |     |     |     | 515 |     |     |     |     | 520 |     |     |     |     | 525 |     |      |
| cgg | aat | gtc | agc | cga | ggc | agg | gaa | tgc | gtg | gac | aag | tgc | aag | ctt | ctg | 1812 |
| Arg | Asn | Val | Ser | Arg | Gly | Arg | Glu | Cys | Val | Asp | Lys | Cys | Lys | Leu | Leu |      |
|     |     |     | 530 |     |     |     |     | 535 |     |     |     |     | 540 |     |     |      |
| gag | ggt | gag | cca | agg | gag | ttt | gtg | gag | aac | tct | gag | tgc | ata | cag | tgc | 1860 |
| Glu | Gly | Glu | Pro | Arg | Glu | Phe | Val | Glu | Asn | Ser | Glu | Cys | Ile | Gln | Cys |      |
|     |     | 545 |     |     |     |     | 550 |     |     |     |     | 555 |     |     |     |      |
| cac | cca | gag | tgc | ctg | cct | cag | gcc | atg | aac | atc | acc | tgc | aca | gga | cgg | 1908 |
| His | Pro | Glu | Cys | Leu | Pro | Gln | Ala | Met | Asn | Ile | Thr | Cys | Thr | Gly | Arg |      |
|     | 560 |     |     |     |     | 565 |     |     |     |     | 570 |     |     |     |     |      |
| gga | cca | gac | aac | tgt | atc | cag | tgt | gcc | cac | tac | att | gac | ggc | ccc | cac | 1956 |
| Gly | Pro | Asp | Asn | Cys | Ile | Gln | Cys | Ala | His | Tyr | Ile | Asp | Gly | Pro | His |      |
| 575 |     |     |     |     | 580 |     |     |     |     | 585 |     |     |     |     | 590 |      |
| tgc | gtc | aag | acc | tgc | ccg | gca | gga | gtc | atg | gga | gaa | aac | aac | acc | ctg | 2004 |
| Cys | Val | Lys | Thr | Cys | Pro | Ala | Gly | Val | Met | Gly | Glu | Asn | Asn | Thr | Leu |      |
|     |     |     |     | 595 |     |     |     |     | 600 |     |     |     |     | 605 |     |      |
| gtc | tgg | aag | tac | gca | gac | gcc | ggc | cat | gtg | tgc | cac | ctg | tgc | cat | cca | 2052 |
| Val | Trp | Lys | Tyr | Ala | Asp | Ala | Gly | His | Val | Cys | His | Leu | Cys | His | Pro |      |
|     |     |     | 610 |     |     |     |     | 615 |     |     |     |     | 620 |     |     |      |
| aac | tgc | acc | tac | gga | tgc | act | ggg | cca | ggt | ctt | gaa | ggc | tgt | cca | acg | 2100 |
| Asn | Cys | Thr | Tyr | Gly | Cys | Thr | Gly | Pro | Gly | Leu | Glu | Gly | Cys | Pro | Thr |      |
|     |     | 625 |     |     |     |     | 630 |     |     |     |     | 635 |     |     |     |      |
| aat | ggg | cct | aag | atc | ccg | tcc | atc | gcc | act | ggg | atg | gtg | ggg | gcc | ctc | 2148 |
| Asn | Gly | Pro | Lys | Ile | Pro | Ser | Ile | Ala | Thr | Gly | Met | Val | Gly | Ala | Leu |      |
|     | 640 |     |     |     |     | 645 |     |     |     |     | 650 |     |     |     |     |      |
| ctc | ttg | ctg | ctg | gtg | gtg | gcc | ctg | ggg | atc | ggc | ctc | ttc | atg | cga | agg | 2196 |
| Leu | Leu | Leu | Leu | Val | Val | Ala | Leu | Gly | Ile | Gly | Leu | Phe | Met | Arg | Arg |      |
| 655 |     |     |     |     | 660 |     |     |     |     | 665 |     |     |     |     | 670 |      |
| cgc | cac | atc | gtt | cgg | aag | cgc | acg | ctg | cgg | agg | ctg | ctg | cag | gag | agg | 2244 |

-continued

| | | | | | | | | | | | | | | | |
|---|---|---|---|---|---|---|---|---|---|---|---|---|---|---|---|
| Arg | His | Ile | Val | Arg | Lys | Arg | Thr | Leu | Arg | Arg | Leu | Leu | Gln | Glu | Arg |
| | | | 675 | | | | 680 | | | | | 685 | | | |

| | | | | | | | | | | | | | | | | |
|---|---|---|---|---|---|---|---|---|---|---|---|---|---|---|---|---|
| gag | ctt | gtg | gag | cct | ctt | aca | ccc | agt | gga | gaa | gct | ccc | aac | caa | gct | 2292 |
| Glu | Leu | Val | Glu | Pro | Leu | Thr | Pro | Ser | Gly | Glu | Ala | Pro | Asn | Gln | Ala | |
| | | | 690 | | | | 695 | | | | | 700 | | | | |

| | | | | | | | | | | | | | | | | |
|---|---|---|---|---|---|---|---|---|---|---|---|---|---|---|---|---|
| ctc | ttg | agg | atc | ttg | aag | gaa | act | gaa | ttc | aaa | aag | atc | aaa | gtg | ctg | 2340 |
| Leu | Leu | Arg | Ile | Leu | Lys | Glu | Thr | Glu | Phe | Lys | Lys | Ile | Lys | Val | Leu | |
| | | | 705 | | | | 710 | | | | | 715 | | | | |

| | | | | | | | | | | | | | | | | |
|---|---|---|---|---|---|---|---|---|---|---|---|---|---|---|---|---|
| ggc | tcc | ggt | gcg | ttc | ggc | acg | gtg | tat | aag | gga | ctc | tgg | atc | cca | gaa | 2388 |
| Gly | Ser | Gly | Ala | Phe | Gly | Thr | Val | Tyr | Lys | Gly | Leu | Trp | Ile | Pro | Glu | |
| | | | 720 | | | | 725 | | | | | 730 | | | | |

| | | | | | | | | | | | | | | | | |
|---|---|---|---|---|---|---|---|---|---|---|---|---|---|---|---|---|
| ggt | gag | aaa | gtt | aaa | att | ccc | gtc | gct | atc | aag | gaa | tta | aga | gaa | gca | 2436 |
| Gly | Glu | Lys | Val | Lys | Ile | Pro | Val | Ala | Ile | Lys | Glu | Leu | Arg | Glu | Ala | |
| 735 | | | | 740 | | | | 745 | | | | 750 | | | | |

| | | | | | | | | | | | | | | | | |
|---|---|---|---|---|---|---|---|---|---|---|---|---|---|---|---|---|
| aca | tct | ccg | aaa | gcc | aac | aag | gaa | atc | ctc | gat | gaa | gcc | tac | gtg | atg | 2484 |
| Thr | Ser | Pro | Lys | Ala | Asn | Lys | Glu | Ile | Leu | Asp | Glu | Ala | Tyr | Val | Met | |
| | | | | 755 | | | | 760 | | | | | 765 | | | |

| | | | | | | | | | | | | | | | | |
|---|---|---|---|---|---|---|---|---|---|---|---|---|---|---|---|---|
| gcc | agc | gtg | gac | aac | ccc | cac | gtg | tgc | cgc | ctg | ctg | ggc | atc | tgc | ctc | 2532 |
| Ala | Ser | Val | Asp | Asn | Pro | His | Val | Cys | Arg | Leu | Leu | Gly | Ile | Cys | Leu | |
| | | | 770 | | | | | 775 | | | | 780 | | | | |

| | | | | | | | | | | | | | | | | |
|---|---|---|---|---|---|---|---|---|---|---|---|---|---|---|---|---|
| acc | tcc | acc | gtg | caa | ctc | atc | acg | cag | ctc | atg | ccc | ttc | ggc | tgc | ctc | 2580 |
| Thr | Ser | Thr | Val | Gln | Leu | Ile | Thr | Gln | Leu | Met | Pro | Phe | Gly | Cys | Leu | |
| | | | | 785 | | | | 790 | | | | | 795 | | | |

| | | | | | | | | | | | | | | | | |
|---|---|---|---|---|---|---|---|---|---|---|---|---|---|---|---|---|
| ctg | gac | tat | gtc | cgg | gaa | cac | aaa | gac | aat | att | ggc | tcc | cag | tac | ctg | 2628 |
| Leu | Asp | Tyr | Val | Arg | Glu | His | Lys | Asp | Asn | Ile | Gly | Ser | Gln | Tyr | Leu | |
| | | | 800 | | | | 805 | | | | | 810 | | | | |

| | | | | | | | | | | | | | | | | |
|---|---|---|---|---|---|---|---|---|---|---|---|---|---|---|---|---|
| ctc | aac | tgg | tgt | gtg | cag | atc | gca | aag | ggc | atg | aac | tac | ttg | gag | gac | 2676 |
| Leu | Asn | Trp | Cys | Val | Gln | Ile | Ala | Lys | Gly | Met | Asn | Tyr | Leu | Glu | Asp | |
| 815 | | | | 820 | | | | 825 | | | | 830 | | | | |

| | | | | | | | | | | | | | | | | |
|---|---|---|---|---|---|---|---|---|---|---|---|---|---|---|---|---|
| cgt | cgc | ttg | gtg | cac | cgc | gac | ctg | gca | gcc | agg | aac | gta | ctg | gtg | aaa | 2724 |
| Arg | Arg | Leu | Val | His | Arg | Asp | Leu | Ala | Ala | Arg | Asn | Val | Leu | Val | Lys | |
| | | | | 835 | | | | 840 | | | | | 845 | | | |

| | | | | | | | | | | | | | | | | |
|---|---|---|---|---|---|---|---|---|---|---|---|---|---|---|---|---|
| aca | ccg | cag | cat | gtc | aag | atc | aca | gat | ttt | ggg | ctg | gcc | aaa | ctg | ctg | 2772 |
| Thr | Pro | Gln | His | Val | Lys | Ile | Thr | Asp | Phe | Gly | Leu | Ala | Lys | Leu | Leu | |
| | | | | 850 | | | | 855 | | | | | 860 | | | |

| | | | | | | | | | | | | | | | | |
|---|---|---|---|---|---|---|---|---|---|---|---|---|---|---|---|---|
| ggt | gcg | gaa | gag | aaa | gaa | tac | cat | gca | gaa | gga | ggc | aaa | gtg | cct | atc | 2820 |
| Gly | Ala | Glu | Glu | Lys | Glu | Tyr | His | Ala | Glu | Gly | Gly | Lys | Val | Pro | Ile | |
| | | | | 865 | | | | 870 | | | | | 875 | | | |

| | | | | | | | | | | | | | | | | |
|---|---|---|---|---|---|---|---|---|---|---|---|---|---|---|---|---|
| aag | tgg | atg | gca | ttg | gaa | tca | att | tta | cac | aga | atc | tat | acc | cac | cag | 2868 |
| Lys | Trp | Met | Ala | Leu | Glu | Ser | Ile | Leu | His | Arg | Ile | Tyr | Thr | His | Gln | |
| | | | 880 | | | | 885 | | | | | 890 | | | | |

| | | | | | | | | | | | | | | | | |
|---|---|---|---|---|---|---|---|---|---|---|---|---|---|---|---|---|
| agt | gat | gtc | tgg | agc | tac | ggg | gtg | acc | gtt | tgg | gag | ttg | atg | acc | ttt | 2916 |
| Ser | Asp | Val | Trp | Ser | Tyr | Gly | Val | Thr | Val | Trp | Glu | Leu | Met | Thr | Phe | |
| 895 | | | | 900 | | | | 905 | | | | 910 | | | | |

| | | | | | | | | | | | | | | | | |
|---|---|---|---|---|---|---|---|---|---|---|---|---|---|---|---|---|
| gga | tcc | aag | cca | tat | gac | gga | atc | cct | gcc | agc | gag | atc | tcc | tcc | atc | 2964 |
| Gly | Ser | Lys | Pro | Tyr | Asp | Gly | Ile | Pro | Ala | Ser | Glu | Ile | Ser | Ser | Ile | |
| | | | | 915 | | | | 920 | | | | | 925 | | | |

| | | | | | | | | | | | | | | | | |
|---|---|---|---|---|---|---|---|---|---|---|---|---|---|---|---|---|
| ctg | gag | aaa | gga | gaa | cgc | ctc | cct | cag | cca | ccc | ata | tgt | acc | atc | gat | 3012 |
| Leu | Glu | Lys | Gly | Glu | Arg | Leu | Pro | Gln | Pro | Pro | Ile | Cys | Thr | Ile | Asp | |
| | | | 930 | | | | 935 | | | | | 940 | | | | |

| | | | | | | | | | | | | | | | | |
|---|---|---|---|---|---|---|---|---|---|---|---|---|---|---|---|---|
| gtc | tac | atg | atc | atg | gtc | aag | tgc | tgg | atg | ata | gac | gca | gat | agt | cgc | 3060 |
| Val | Tyr | Met | Ile | Met | Val | Lys | Cys | Trp | Met | Ile | Asp | Ala | Asp | Ser | Arg | |
| | | | | 945 | | | | 950 | | | | | 955 | | | |

| | | | | | | | | | | | | | | | | |
|---|---|---|---|---|---|---|---|---|---|---|---|---|---|---|---|---|
| cca | aag | ttc | cgt | gag | ttg | atc | atc | gaa | ttc | tcc | aaa | atg | gcc | cga | gac | 3108 |
| Pro | Lys | Phe | Arg | Glu | Leu | Ile | Ile | Glu | Phe | Ser | Lys | Met | Ala | Arg | Asp | |
| | | | 960 | | | | 965 | | | | | 970 | | | | |

| | | | | | | | | | | | | | | | | |
|---|---|---|---|---|---|---|---|---|---|---|---|---|---|---|---|---|
| ccc | cag | cgc | tac | ctt | gtc | att | cag | ggg | gat | gaa | aga | atg | cat | ttg | cca | 3156 |
| Pro | Gln | Arg | Tyr | Leu | Val | Ile | Gln | Gly | Asp | Glu | Arg | Met | His | Leu | Pro | |
| 975 | | | | 980 | | | | 985 | | | | | 990 | | | |

```
agt cct aca gac tcc aac ttc tac cgt gcc ctg atg gat gaa gaa gac    3204
Ser Pro Thr Asp Ser Asn Phe Tyr Arg Ala Leu Met Asp Glu Glu Asp
            995                 1000                1005 atg gac gac gtg gtg gat gcc gac gag tac ctc atc cca cag cag ggc    3252
Met Asp Asp Val Val Asp Ala Asp Glu Tyr Leu Ile Pro Gln Gln Gly
        1010                1015                1020 ttc ttc agc agc ccc tcc acg tca cgg act ccc ctc ctg agc tct ctg    3300
Phe Phe Ser Ser Pro Ser Thr Ser Arg Thr Pro Leu Leu Ser Ser Leu
    1025                1030                1035 agt gca acc agc aac aat tcc acc gtg gct tgc att gat aga aat ggg    3348
Ser Ala Thr Ser Asn Asn Ser Thr Val Ala Cys Ile Asp Arg Asn Gly
1040                1045                1050 ctg caa agc tgt ccc atc aag gaa gac agc ttc ttg cag cga tac agc    3396
Leu Gln Ser Cys Pro Ile Lys Glu Asp Ser Phe Leu Gln Arg Tyr Ser
1055                1060                1065                1070 tca gac ccc aca ggc gcc ttg act gag gac agc ata gac gac acc ttc    3444
Ser Asp Pro Thr Gly Ala Leu Thr Glu Asp Ser Ile Asp Asp Thr Phe
            1075                1080                1085 ctc cca gtg cct gaa tac ata aac cag tcc gtt ccc aaa agg ccc gct    3492
Leu Pro Val Pro Glu Tyr Ile Asn Gln Ser Val Pro Lys Arg Pro Ala
        1090                1095                1100 ggc tct gtg cag aat cct gtc tat cac aat cag cct ctg aac ccc gcg    3540
Gly Ser Val Gln Asn Pro Val Tyr His Asn Gln Pro Leu Asn Pro Ala
    1105                1110                1115 ccc agc aga gac cca cac tac cag gac ccc cac agc act gca gtg ggc    3588
Pro Ser Arg Asp Pro His Tyr Gln Asp Pro His Ser Thr Ala Val Gly
1120                1125                1130 aac ccc gag tat ctc aac act gtc cag ccc acc tgt gtc aac agc aca    3636
Asn Pro Glu Tyr Leu Asn Thr Val Gln Pro Thr Cys Val Asn Ser Thr
1135                1140                1145                1150 ttc gac agc cct gcc cac tgg gcc cag aaa ggc agc cac caa att agc    3684
Phe Asp Ser Pro Ala His Trp Ala Gln Lys Gly Ser His Gln Ile Ser
            1155                1160                1165 ctg gac aac cct gac tac cag cag gac ttc ttt ccc aag gaa gcc aag    3732
Leu Asp Asn Pro Asp Tyr Gln Gln Asp Phe Phe Pro Lys Glu Ala Lys
        1170                1175                1180 cca aat ggc atc ttt aag ggc tcc aca gct gaa aat gca gaa tac cta    3780
Pro Asn Gly Ile Phe Lys Gly Ser Thr Ala Glu Asn Ala Glu Tyr Leu
    1185                1190                1195 agg gtc gcg cca caa agc agt gaa ttt att gga gca tga ccacggagga    3829
Arg Val Ala Pro Gln Ser Ser Glu Phe Ile Gly Ala
1200                1205                1210 tagtatgagc cctaaaaatc cagactcttt cgatacccag gaccaagcca cagcaggtcc    3889
tccatcccaa cagccatgcc cgcattagct cttagaccca cagactggtt ttgcaacgtt    3949
tacaccgact agccaggaag tacttccacc tcgggcacat tttgggaagt tgcattcctt    4009
tgtcttcaaa ctgtgaagca tttacagaaa cgcatccagc aagaatattg tccctttgag    4069
cagaaattta tctttcaaag aggtatattt gaaaaaaaaa aaaaagtat atgtgaggat    4129 ttttattgat tggggatctt ggagtttttc attgtcgcta ttgatttta cttcaatggg    4189 ctcttccaac aaggaagaag cttgctggta gcacttgcta ccctgagttc atccaggccc    4249
aactgtgagc aaggagcaca agccacaagt cttccagagg atgcttgatt ccagtggttc    4309
tgcttcaagg cttccactgc aaaacactaa agatccaaga aggccttcat ggccccagca    4369
ggccggatcg gtactgtatc aagtcatggc aggtacagta ggataagcca ctctgtccct    4429
tcctgggcaa agaagaaacg gaggggatga attcttcctt agacttactt ttgtaaaaat    4489
gtccccacgg tacttactcc ccactgatgg accagtggtt tccagtcatg agcgttagac    4549
```

-continued

```
tgacttgttt gtcttccatt ccattgtttt gaaactcagt atgccgcccc tgtcttgctg    4609
tcatgaaatc agcaagagag gatgacacat caaataataa ctcggattcc agcccacatt    4669
ggattcatca gcatttggac caatagccca cagctgagaa tgtggaatac ctaaggataa    4729
caccgctttt gttctcgcaa aaacgtatct cctaatttga ggctcagatg aaatgcatca    4789
ggtcctttgg ggcatagatc agaagactac aaaaatgaag ctgctctgaa atctccttta    4849
gccatcaccc caaccccca aaattagttt gtgttactta tggaagatag ttttctcctt    4909
ttacttcact tcaaaagctt tttactcaaa gagtatatgt tccctccagg tcagctgccc    4969
ccaaaccccc tccttacgct tgtcacaca aaaagtgtct ctgccttgag tcatctattc    5029
aagcacttac agctctggcc acaacagggc attttacagg tgcgaatgac agtagcatta    5089
tgagtagtgt gaattcaggt agtaaatatg aaactagggt ttgaaattga taatgctttc    5149
acaacatttg cagatgtttt agaaggaaaa aagttccttc ctaaaataat ttctctacaa    5209
ttggaagatt ggaagattca gctagttagg agcccatttt ttcctaatct gtgtgtgccc    5269
tgtaacctga ctggttaaca gcagtccttt gtaaacagtg ttttaaactc tcctagtcaa    5329
tatccacccc atccaattta tcaaggaaga aatggttcag aaaatatttt cagcctacag    5389
ttatgttcag tcacacacac atacaaaatg ttccttttgc ttttaaagta atttttgact    5449
cccagatcag tcagagcccc tacagcattg ttaagaaagt atttgatttt tgtctcaatg    5509
aaaataaaac tatattcatt tcc                                            5532
```

<210> SEQ ID NO 2
<211> LENGTH: 1210
<212> TYPE: PRT
<213> ORGANISM: Homo sapiens

<400> SEQUENCE: 2

```
Met Arg Pro Ser Gly Thr Ala Gly Ala Ala Leu Leu Ala Leu Leu Ala
  1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190
```

-continued

```
Ser Cys Pro Asn Gly Ser Cys Trp Gly Ala Gly Glu Asn Cys Gln
    195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
```

-continued

```
            610                 615                 620
Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
                930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                1000                1005

Asp Val Val Asp Ala Asp Glu Tyr Leu Ile Pro Gln Gln Gly Phe Phe
                1010                1015                1020

Ser Ser Pro Ser Thr Ser Arg Thr Pro Leu Leu Ser Ser Leu Ser Ala
1025                1030                1035                1040
```

-continued

```
Thr Ser Asn Asn Ser Thr Val Ala Cys Ile Asp Arg Asn Gly Leu Gln
            1045                1050                1055

Ser Cys Pro Ile Lys Glu Asp Ser Phe Leu Gln Arg Tyr Ser Ser Asp
        1060                1065                1070

Pro Thr Gly Ala Leu Thr Glu Asp Ser Ile Asp Asp Thr Phe Leu Pro
    1075                1080                1085

Val Pro Glu Tyr Ile Asn Gln Ser Val Pro Lys Arg Pro Ala Gly Ser
 1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
        1140                1145                1150

Ser Pro Ala His Trp Ala Gln Lys Gly Ser His Gln Ile Ser Leu Asp
    1155                1160                1165

Asn Pro Asp Tyr Gln Gln Asp Phe Phe Pro Lys Glu Ala Lys Pro Asn
 1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

<210> SEQ ID NO 3
<211> LENGTH: 3982
<212> TYPE: DNA
<213> ORGANISM: Artificial Sequence
<220> FEATURE:
<223> OTHER INFORMATION: Description of Artificial Sequence: Plasmid
      pNGVL1

<400> SEQUENCE: 3
tggccattgc atacgttgta tccatatcat aatatgtaca tttatattgg ctcatgtcca      60
acattaccgc catgttgaca ttgattattg actagttatt aatagtaatc aattacgggg     120
tcattagttc atagcccata tatggagttc cgcgttacat aacttacggt aaatggcccg     180
cctggctgac cgcccaacga cccccgccca ttgacgtcaa taatgacgta tgttcccata     240
gtaacgccaa tagggacttt ccattgacgt caatgggtgg agtatttacg gtaaactgcc     300
cacttggcag tacatcaagt gtatcatatg ccaagtacgc cccctattga cgtcaatgac     360
ggtaaatggc ccgcctggca ttatgcccag tacatgacct tatgggactt tcctacttgg     420
cagtacatct acgtattagt catcgctatt accatggtga tgcggttttg gcagtacatc     480
aatgggcgtg atagcggttt gactcacggg gatttccaa gtctccaccc cattgacgtc     540
aatgggagtt tgttttggca ccaaaatcaa cgggactttc caaaatgtcg taacaactcc     600
gccccattga cgcaaatggg cggtaggcgt gtacggtggg aggtctatat aagcagagct     660
cgtttagtga accgtcagat cgcctggaga cgccatccac gctgttttga cctccataga     720
agacaccggg accgatccag cctccgcggc cgggaacggt gcattggaac gcggattccc     780
cgtgccaaga gtgacgtaag taccgcctat agagtctata ggcccacccc cttggcttct     840
tatgcatgct atactgtttt tggcttgggg tctatacacc cccgcttcct catgttatag     900
gtgatggtat agcttagcct ataggtgtgg gttattgacc attattgacc actccaacgg     960
tggagggcag tgtagtctga gcagtactcg ttgctgccgc gcgcgccacc agacataata    1020
```

```
gctgacagac taacagactg ttcctttcca tgggtctttt ctgcagtcac cgtcgtcgac    1080
ggtatcgata agcttgatat cagatctttt tccctctgcc aaaaattatg gggacatcat    1140
gaagcccctt gagcatctga cttctggcta ataaaggaaa tttatttcat tgcaatagtg    1200
tgttggaatt ttttgtgtct ctcactcgga aggacatatg ggagggcaaa tcatttaaaa    1260
catcagaatc agtatttggt ttagagtttg caacatatg ccattcttcc gcttcctcgc    1320
tcactgactc gctgcgctcg gtcgttcggc tgcggcgagc ggtatcagct cactcaaagg    1380
cggtaatacg gttatccaca gaatcagggg ataacgcagg aaagaacatg tgagcaaaag    1440
gccagcaaaa ggccaggaac cgtaaaaagg ccgcgttgct ggcgtttttc cataggctcc    1500
gcccccctga cgagcatcac aaaaatcgac gctcaagtca gaggtggcga acccgacag    1560 gactataaag ataccaggcg tttccccctg gaagctccct cgtgcgctct cctgttccga    1620
ccctgccgct taccggatac ctgtccgcct ttctcccttc gggaagcgtg cgctttctc    1680 aatgctcacg ctgtaggtat ctcagttcgg tgtaggtcgt tcgctccaag ctgggctgtg    1740
tgcacgaacc ccccgttcag cccgaccgct gcgccttatc cggtaactat cgtcttgagt    1800
ccaacccggt aagacacgac ttatcgccac tggcagcagc cactggtaac aggattagca    1860
gagcgaggta tgtaggcggt gctacagagt tcttgaagtg gtggcctaac tacggctaca    1920
ctagaaggac agtatttggt atctgcgctc tgctgaagcc agttaccttc ggaaaaagag    1980
ttggtagctc ttgatccggc aaacaaacca ccgctggtag cggtggtttt tttgtttgca    2040
agcagcagat tacgcgcaga aaaaaaggat ctcaagaaga tcctttgatc ttttctacgg    2100
ggtctgacgc tcagtggaac gaaaactcac gttaagggat tttggtcatg agattatcaa    2160
aaaggatctt cacctagatc cttttaaatt aaaaatgaag ttttaaatca atctaaagta    2220
tatatgagta aacttggtct gacagttacc aatgcttaat cagtgaggca cctatctcag    2280
cgatctgtct atttcgttca tccatagttg cctgactcgg ggggggggg cgctgaggtc    2340 tgcctcgtga agaaggtgtt gctgactcat accaggcctg aatcgcccca tcatccagcc    2400
agaaagtgag ggagccacgg ttgatgagag ctttgttgta ggtggaccag ttggtgattt    2460
tgaacttttg ctttgccacg gaacggtctg cgttgtcggg aagatgcgtg atctgatcct    2520
tcaactcagc aaaagttcga tttattcaac aaagccgccg tcccgtcaag tcagcgtaat    2580
gctctgccag tgttacaacc aattaaccaa ttctgattag aaaaactcat cgagcatcaa    2640
atgaaactgc aatttattca tatcaggatt atcaatacca tttttgaa aaagccgttt    2700 ctgtaatgaa ggagaaaact caccgaggca gttccatagg atggcaagat cctggtatcg    2760
gtctgcgatt ccgactcgtc caacatcaat acaacctatt aatttcccct cgtcaaaaat    2820
aaggttatca agtgagaaat caccatgagt gacgactgaa tccggtgaga atggcaaaag    2880
cttatgcatt tctttccaga cttgttcaac aggccagcca ttacgctcgt catcaaaatc    2940
actcgcatca accaaaccgt tattcattcg tgattgcgcc tgagcgagac gaaatacgcg    3000
atcgctgtta aaaggacaat acaaacagg aatcgaatgc aaccggcgca ggaacactgc    3060
cagcgcatca acaatatttt cacctgaatc aggatattct tctaataacct ggaatgctgt    3120 tttccggg atcgcagtgg tgagtaacca tgcatcatca ggagtacgga taaaatgctt    3180
gatggtcgga agaggcataa attccgtcag ccagtttagt ctgaccatct catctgtaac    3240
atcattggca acgctacctt tgccatgttt cagaaacaac tctggcgcat cgggcttccc    3300
atacaatcga tagattgtcg cacctgattg cccgacatta tcgcgagccc atttataccc    3360
atataaatca gcatccatgt tggaatttaa tcgcggcctc gagcaagacg tttcccgttg    3420
```

```
aatatggctc ataacacccc ttgtattact gtttatgtaa gcagacagtt ttattgttca    3480
tgatgatata tttttatctt gtgcaatgta acatcagaga ttttgagaca caacgtggct    3540 ttccccoccc ccccattatt gaagcattta tcagggttat tgtctcatga gcggatacat    3600
atttgaatgt atttagaaaa ataaacaaat aggggttccg cgcacatttc cccgaaaagt    3660
gccacctgac gtctaagaaa ccattattat catgacatta acctataaaa ataggcgtat    3720
cacgaggccc tttcgtcctc gcgcgtttcg gtgatgacgg tgaaaacctc tgacacatgc    3780
agctcccgga gacggtcaca gcttgtctgt aagcggatgc cggagcaga caagcccgtc     3840 agggcgcgtc agcgggtgtt ggcgggtgtc ggggctggct taactatgcg gcatcagagc    3900
agattgtact gagagtgcac catatgcggt gtgaaatacc gcacagatgc gtaaggagaa    3960
aataccgcat cagattggct at                                            3982

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: antisense
      EGFR sequence

<400> SEQUENCE: 4
ccggccgtcc cggagggtcg gatcgctgct ccccgaag                              38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: sense EGFR
      sequence

<400> SEQUENCE: 5
cttcggggag cagcgatgcg accctccggg acggccgg                              38
```

INHIBITION OF HUMAN SQUAMOUS CELL CARCINOMA GROWTH IN VIVO BY EPIDERMAL GROWTH FACTOR RECEPTOR ANTISENSE RNA TRANSCRIBED FROM A POL III PROMOTER

This application is a divisional of U.S. patent application Ser. No. 09/595,863, filed Jun. 16, 2000, now abandoned, which claimed priority to U.S. Provisional Patent Application No. 60/140,136, filed Jun. 18, 1999, all of which are herein incorporated by reference.

The U.S. Government has a paid-up license in this invention and the right in limited circumstances to require the patent owner to license others on reasonable terms of Grant Nos. CA64654, CA71730, CA01760 and CA72526 awarded by the National Cancer Institute, National Institutes of Health.

BACKGROUND OF THE INVENTION

Epidermal growth factor receptor (EGFR) (HER I) is a member of the tyrosine kinase family (Type 1) of cell surface receptors, for which several peptide ligands have been reported, including epidermal growth factor (EGF), transforming growth factor-α (TGF-α), vaccinia growth factor, amphiregulin, and cripto. Ligand binding to EGFR stimulates mitogenesis, and overexpression of EGFR has been associated with increased tumor growth, metastasis, and/or adverse outcome in numerous epithelial cancers, including squamous cell carcinomas of the head and neck (SCCHN) (1,2). Many human tumor cells express high levels of EGFR, raising the possibility that receptor-directed therapies may be useful as anticancer strategies. Such treatment has included monoclonal antibodies directed against EGFR (3-6) or fusion proteins/immunotoxins against TGF-α/EGFR using toxins elaborated by Pseudomonas or Diphtheria species (7,8).

EGFR antisense-expression plasmids have been shown to block translation of EGFR messenger RNA (mRNA) and suppress the transforming phenotype of pharyngeal carcinoma (KB) cells in vitro (9). Targeting EGFR via several different approaches, including suppression of EGFR mRNA using anti-sense oligonucleotides, and blocking the function of the mature protein at two sites, the ligand-binding domain and the kinase domain, we previously demonstrated inhibition of proliferation of SCCHN but not normal mucosal squamous epithelial cells (10). Nevertheless, due to the inherent unpredicatbility in antisense technology and the inability to extend in vitro findings to in vivo in antisense therapies, an effective in vivo antisense therapy is desired.

SUMMARY OF THE INVENTION

It is therefore an object of the present invention to provide a gene transfer vector that can: 1) transfect a large proportion of tumor cells in vivo; 2) generate high expression levels of antisense RNA in each cell; and 3) demonstrate an antitumor response following treatment.

The present invention provides a gene therapy vector for the in vivo reduction of EGFR expression. The vector is a nucleic acid comprising an expression cassette which includes transcription control sequences of a member of a class of Pol III-transcribed genes in which no transcribed portion of the Pol III gene is required for transcription of the gene. In the expression cassette, the transcribed 5' hairpin structure of the Pol III gene is deleted. The transcription control sequences are operably linked to a sequence of an EGFR gene in an antisense orientation suitable for decreasing expression of EGFR in the cell when transcribed. The transcription control sequences typically are transcription control sequences of the human U6 snRNP gene. The antisense EGFR nucleic acid preferably spans either the translation start site of the EGFR coding region or RNA splice junctions thereof. The vector typically is included in a composition including a suitable pharmaceutical excipient for the in vivo delivery of the vector to target cells, typically cancer cells. The excipient can be a cationic liposome, preferably a DC-Chol liposome, that accelerates the passage of the vector into target cells.

The present invention also includes a method for decreasing expression of EGFR in cells, such as for treatment of SCCHN, that includes contacting a target cell with the above-described pharmaceutical composition to cause passage of the vector into the target cell, resulting in expression of the antisense RNA.

Accordingly, the compositions and methods of the present invention provide high levels of expression of antisense EGFR RNA that can effectively reduce expression of endogenous EGFR in cells, and provide sustained tumor growth inhibition in vivo.

BRIEF DESCRIPTION OF THE DRAWINGS

The file of this patent contains at least one drawing executed in color. Copies of this patent with color drawing(s) will be provided by the Patent and Tradmark Office upon request and payment of the necessary fee.

FIG. 3A is a photograph of an ethidium bromide staining of a polymerase chain reaction gel demonstrating endogenous U6 RNA in a representative control tumor (treated with liposomes alone), sense-, and antisense-treated tumors. FIG. 3B is an autoradiograph of the same gel following hybridization with the oligonucleotide probes for the EGFR region of the U6/antisense or U6/sense chimeric DNA. The chimeric RNA is detected in the tumors treated with DNA plus liposomes but not in the control.

FIGS. 5A-C are photomicrographs showing epidermal growth factor receptor immunostaining in a representative tumor: FIG. 5A shows tumor cells treated with liposomes alone (control), FIG. 5B illustrates the consequences of treatment with the sense construct plus liposomes, and FIG. 5C shows staining in a representative antisense plus liposome-treated tumor.

FIGS. 8A-C are photomicrographs that represent Apotaq staining of treated tumors, where FIG. 5A shows a representative control tumor stained for DNA fragmentation, FIG. 5B shows a representative sense-treated tumor, and FIG. 5C shows a typical antisense-treated tumor.

FIG. 9 shows the nucleotide sequence of the human mRNA for precursor of the EGFR, GenBank Accession No. X00588 (SEQ ID NO: 1).

FIG. 10 shows the nucleotide sequence of pGVL1 (SEQ ID NO: 3).

FIG. 11 is map of the plasmid pNGVL1-EGFR-AS.

DETAILED DESCRIPTION OF THE PREFERRED EMBODIMENTS

Figure 1:
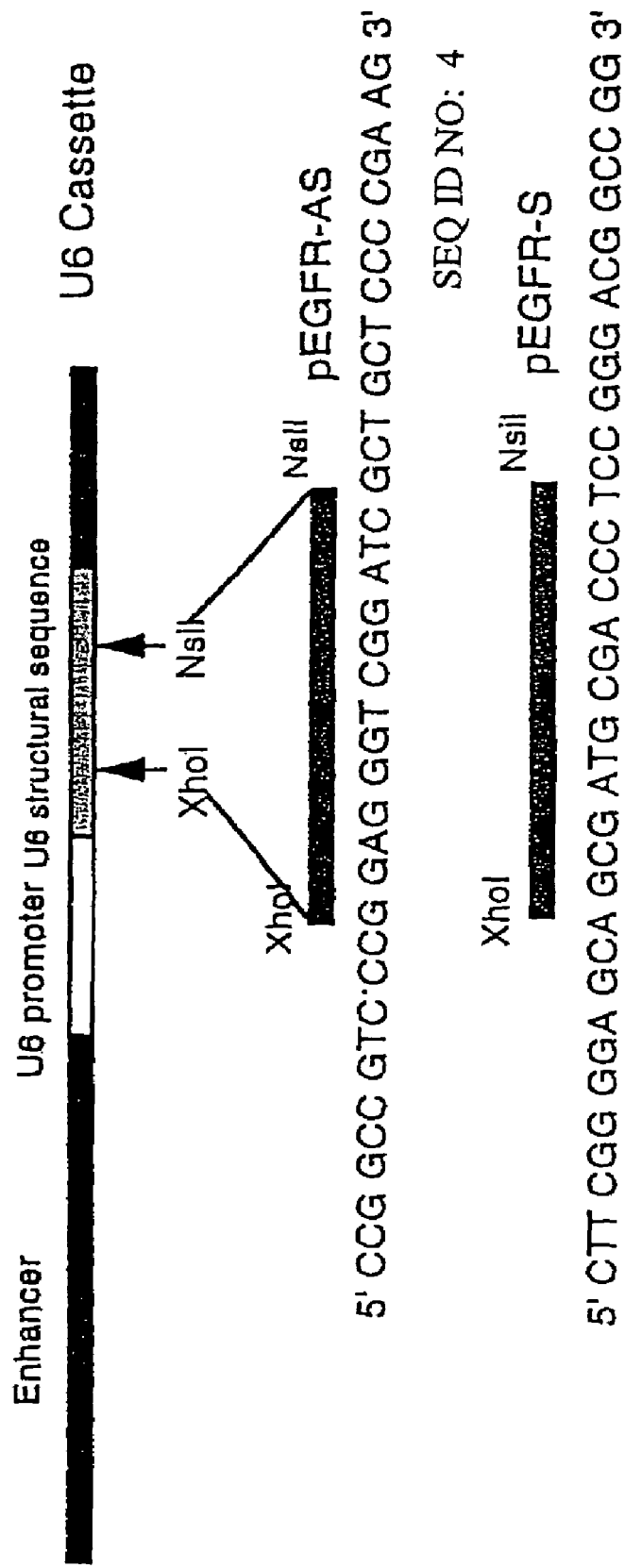
FIG. 1 is a schematic representation of the U6 expression cassette in the pGEM vector showing the EGFR antisense and sense oligonucleotide sequences.

Other than in the operating examples, or where otherwise indicated, all numbers or expressions referring to quantities of ingredients, reaction conditions, etc, used in the specification and claims are to be understood as modified in all instances by the term "about."

The present invention includes a nucleic acid vector for the in vivo modulation of EGFR expression. When introduced into a cell that expresses EGFR, the vector produces antisense RNA (antisense EGFR RNA) directed to a portion of native (endogenous) EGFR mRNA, that causes a decrease in the expression of the native EGFR in that cell. In certain cells, such as certain tumor-forming cells that over-express EGFR, and more specifically SCCHN cells, this production of antisense EGFR RNA causes reduction of tumor size.

The vector is a nucleic acid comprising an expression cassette which includes transcription control sequences of a member of a class of Pol III-transcribed genes in which no transcribed portion of the Pol III gene is required for transcription of the gene. In the expression cassette, the transcribed 5' hairpin structure of the Pol III gene is deleted. The transcription control sequences are operably linked to a sequence of an EGFR gene in an antisense orientation suitable for decreasing expression of EGFR in the cell when transcribed.

As used herein the phrase "expression cassette" is a nucleic acid that includes transcription control sequences and a nucleic acid sequence that is transcribed and that is operably linked to the transcription control sequences.

As used herein, and as a non-limiting example, in the plasmid pΔHU6-EAS, the EGFR antisense RNA is the transcribed nucleic acid sequence, while the U6 enhancer and promoter sequences are transcription control sequences.

As used herein, "transcription control sequences" are sequences that influence the ultimate levels of antisense RNA in a target cell. These sequences may influence the rate of, and tissue specificity of, transcription and post-transcriptional events in a given cell. Non-limiting examples of these sequences are promoters and enhancers. These transcription control sequences preferably allow for high levels of constitutive expression of the RNA, but may be selected to exhibit controlled, and even tissue-specific expression, as desired.

As a non-limiting example, in the plasmid pΔHU6-EAS, described in detail below, the EGFR antisense RNA is the transcribed nucleic acid sequence, while the U6 enhancer and promoter sequences are transcription control sequences.

The transcription control sequences are derived from an a typical class of Pol III genes in which no transcribed portion of the Pol III gene is required for transcription of the gene. These Pol III genes are more akin to Pol II genes in their lack of transcription control elements in the transcribed sequences, unlike typical Pol III genes. Members of this class of Pol III genes include, without limitation, the U6 gene, the 7SK gene, the H1 RNA gene, the plant U3 snRNA and the MRP gene. The expression cassette may include recombinant derivatives of the described transcription control regions which include transcription control sequences derived from more than one of the above-referenced Pol III genes. Examples of these expression cassettes are described in U.S. Pat. No. 5,624,803. The benefits arising from the use of these a typical Pol III transcription control sequences are the combination of high, typically constitutive transcription rates, with no need to include transcription control sequences in the transcribed sequences.

In contrast to the expression cassettes described in U.S. Pat. No. 5,624,803, the expression cassette of the present invention excludes specifically the 5' hairpin loop (cap) structure of the Pol III gene. It was conventionally thought that the 5' hairpin loop in the transcribed RNA is required for stability of the RNA (see, for example U.S. Pat. No. 5,624,803). For example, previous studies (38, 39) have demonstrated that the first 24 nucleotides in the U6 snRNA that can form a hairpin loop are required for the post-transcriptional modification and thus the stability of the U6 snRNA. However, it now has been found that deletion of this domain does not decrease the amount of chimeric RNA expression in the cell. Since the 5' end hairpin loop could theoretically affect the accessibility of the antisense RNA to the target, this domain was deleted to generate a novel expression vector. The results shown herein verify that the U6 expression vector without a 5' hairpin loop is stable and can generate a large amount of U6/chimeric antisense RNA intracellularly.

The transcribed antisense EGFR sequences typically range in length from about 20 to about 300 nucleotides in length. The transcribed sequences are typically less than about 75 nucleotides in length. The portions of the EGFR gene to which the transcribed antisense sequences are complementary vary. Typically, the antisense sequences are complementary to splice junctions or, preferably, to the ATG start site of the human EGFR mRNA shown in FIG. 9 (SEQ ID NO: 1). Examples of antisense EGFR nucleic acids include those described in U.S. Pat. No. 5,914,269 (including sequences complementary to nucleotides 645-664, nucleotides 769-788, nucleotides 832-851, nucleotides 1110-1129, nucleotides 1761-1780 and nucleotides 2966-2985 of SEQ ID NO: 1) and sequences spanning the ATG start sequence, as described herein.

The expression cassette typically is propagated as part of a nucleic acid vector, typically a plasmid in bacteria. When the vector is a plasmid, the plasmid may be selected from any of the many plasmids that are available in the art. In one embodiment, described below, the plasmid backbone is pGEM2, a broadly available plasmid vector (11). In a second embodiment, also described below, the plasmid is pNGVL1-EGFR-AS (SEQ ID NO: 3), which has been deposited under the Budapest Treaty in the American Type Culture Collection (ATCC) depository located at 10801 University Boulevard, Manassas, Va. 20110-2209, on Aug. 23, 2006, and has Accession Number PTA-7774. The pNGVL1-EGFR-AS plasmid also is available from the National Gene Vector Laboratory at the University of Michigan. The nucleotide sequence of pNGVL1-EGFR-AS is provided in FIG. 10. The plasmid pNGVL1-EGFR-AS is preferred for human use, since the plasmid includes the kanamycin resistance gene, as opposed to the ampicillin resistance gene of the pGEM2 vector. Nevertheless, there are many reasonable substitutions for the pNGVL1-EGFR-AS and pGEM2 plasmids including, without limitation bacterial, yeast, and viral vectors. The vector for propagating the expression cassette preferably is free of nucleotide sequences that enable the vector and the expression cassette to integrate into the genome of the target cells.

The nucleic acid comprising the antisense EGFR expression cassette of the present invention typically is administered to a patient as part of a pharmaceutically acceptable composition that includes the nucleic acid and one or more suitable excipients (drug vehicle) that may facilitate administration of the nucleic acid to the target cell. The choice of excipient typically depends upon the mode of administration of the composition. Examples of suitable excipients are buffers and/or ionic liquids, such as phosphate-buffered saline (PBS).

In one embodiment of the present invention, the pharmaceutical composition includes a cationic liposome or liposome-forming substance complexed with the nucleic acid. By "liposome-forming substance," it is meant that the composition includes one or more materials that, when diluted in an aqueous environment, typically in vivo, the composition forms a liposome. More commonly, the liposomes are preformed and are afterward complexed with the nucleic acid. Other ingredients of the pharmaceutical composition may be added at any time prior to or following the formation of the liposomes and/or the complexing of the liposomes with the nucleic acid. As used herein, the term "pharmaceutical" includes veterinary.

The cationic liposomes may be one of many cationic liposome compositions known in the art. These liposome include Lipofectamine, commercially available from Life Technologies, Inc. A preferred liposome is a DC-Chol liposome, described in U.S. Pat. Nos. 5,795,587 and 6,008,202. These liposomes typically are prepared from a mixture of DC-Chol (3β[N-(N',N'-dimethylaminoethane)-carbamoyl] cholesterol) and DOPE (1,2-dioleoyl-sn-glycero-3-phosphatidylethanolamine) (16).

The pharmaceutical composition of the present invention typically is administered parenterally. The composition commonly is injected intratumorally, or into adjacent tissue. Optionally, the composition may be injected intramuscularly or intravenously. Depending upon the site of administration of the composition and other factors that affect the efficiency of expression (i.e., the down-modulation of EGFR expression) of the antisense RNA, the amount of the nucleic acid containing the expression cassette that is administered may vary broadly.

The present invention is more particularly described in the following examples, which are intended to be illustrative only, since numerous modifications and variations therein will be apparent to those skilled in the art. Unless otherwise specified, all parts and percentages are by weight.

Materials and Methods

Plasmid Construct and Cloning.

In the original U6 expression plasmid (pGEMmU6; from S. Noonberg, University of California San Francisco Cancer Research Institute), the U6 expression cassette contains the U6 promoter, enhancer, and the mutated U6 structural sequence (11). The first 24 and the last 18 nucleotides of the U6 structural sequence remain, while the middle region has been replaced with a 38-base-pair (bp) oligonucleotide fragment containing Xho I and Nsi I sites for convenient cloning. The U6 RNA produced from this vector contains a hairpin loop motif at the 5' end that is responsible for capping of the U6 RNA. Since it has been recently demonstrated that capping of transcripts is not required for nuclear retention (13), we eliminated the sequences containing this motif (from nucleotide 7-24 by polymerase chain reaction (PCR)-mediated deletion) to minimize the flanking sequence around the antisense gene. Forty-bp long sense and antisense oligonucleotides corresponding to the ATG start site of the human EGFR gene (−20 to +20) were synthesized and cloned into the Xho I and Nsi I sites of the new plasmid, pΔHU6, and the sequences were verified by sequence analysis (FIG. 1).

Cells and Tumors.

The cell line, 1483, is a well-described SCCHN cell line derived from a tumor of the retromolar trigone region of the oropharynx (14) from R. Lotan (The University of Texas M. D. Anderson Cancer Center, Houston). It was previously demonstrated that 1483 cells express approximately $5\times10^5$ EGF receptors/cell (10). The cells were maintained in vitro in Dulbecco's modification of Eagle' medium (DMEM) (Fisher Scientific Co., Pittsburgh, Pa.) and were supplemented with 10% fetal calf serum (FCS) and antibiotics (Life Technologies, Inc., Gaithersburg, Md.).

In Vivo Tumor Xenograft Studies.

The 1483 cell line reportedly grows well as xenografts in nude mice (15). Cells in log phase (1483) were harvested by trypsinization, resuspended in DMEM media supplemented with 10% FCS, centrifuged at 1000 rpm for 10 minutes and resuspended in culture media at a concentration of $1\times10^7$ cells/mL prior to subcutaneous implantation into mice. Female athymic nude mice nu/nu (4-6 weeks old; 20±2 g [standard deviation]; Harlan Sprague-Dawley, Inc., Indianapolis, Ind.) were implanted with $1\times10^6$ cells into the right flank with a 26-gauge needle/1 mL tuberculin syringe. Approximately 14-21 days later when the tumor nodules were palpable (~2×2 mm in diameter), mice were randomly assigned to treatment groups (liposomes alone, pΔHU6-EAS [EGFR antisense U6 construct] alone, pΔHU6-EAS plus liposomes, or pΔHU6-ES [EGFR sense U6 construct] plus liposomes). There were 8 to 10 mice in each treatment group in an individual experiment, experiments were repeated three times to insure reproducibility. Intratumoral injection of plasmid DNA (50 μg) complexed with DC-Chol liposomes (50 nmol) in a volume of 50 μL (three times a week for 19 days) was instituted approximately 14-21 days after tumor implantation or when the tumors were palpable (~2×2 mm). Tumors were measured using calipers prior to each injection (three times a week) and tumor volumes were calculated (tumor volume=length×width$^2$/2; fractional tumor volume calculated as a proportion of the pretreatment tumor volume). Mice where killed when the tumors ulcerated or reached a maximum diameter of 2 cm.

Transfection.

In vitro transient transfection was accomplished using plasmid DNA (3 μg) complexed with lipofectamine (10 μg/mL) (Life Technologies, Inc.) according to the manufacturer's instructions. DC-Chol liposomes were prepared by our laboratory for in vivo delivery of plasmid DNA as described (16).

Reverse-transcription-polymerase Chain Reaction (RT-PCR).

To detect the U6 antisense chimeric RNA in the tumor following intratumoral injection of the plasmid-liposome complex, total RNA was extracted from the harvested xenografts as described previously (12). One microgram of the total RNA was digested with 1U of ribonuclease (RNase)-free deoxyribonuclease (DNase) (Life Technologies, Inc.). Complementary DNA (cDNA) was synthesized using avian myeloblastosis virus (AMV) reverse transcriptase and the backward primer complementary to the 3' end of the U6 RNA and U6/antisense chimeric RNA using Access RT-PCR Kit (Promega Corp., Madison, Wis.). PCR was performed on the cDNA using the primers for U6 RNA and U6 chimeric RNA under the conditions recommended by the manufacturer. The PCR products were fractionated on a 12% polyacrylamide gel electrophoresis (PAGE) gel and blotted to nitrocellulose membrane (MSI, Westboro, Mass.). Hybridization of the blot with $^{32}$P-labeled EGFR oligonucleotides was performed as described previously (17). To make sure that the fragment amplified by PCR was not due to residual DNA contamination, PCR was also performed under the same conditions on the RNase-free DNase-treated RNA samples without adding the AMV reverse transcriptase.

Immunoblotting.

Fresh tissue or cell lines were lysed in detergent containing 1% NP-40, 0.1 mM phenylmethyl sulfonyl fluoride, 1 mg/mL leupeptin, and 1 mg/mL aprotinin, and protein levels were determined using the Bio-Rad Protein Assay method (Bio-Rad Laboratories, Hercules, Calif.). Fifty micrograms of total protein was separated on a 10% sodium dodecyl sulfate-PAGE and transferred to nitrocellulose membranes using semi-wet blotting. Filters were blocked with a 5% bovine serum albumin/Tris-buffered saline with Tween 20 (TBST) solution overnight, rinsed three times in TBST, and incubated 90 minutes with a mouse anti-human EGFR monoclonal antibody (Transduction Labs, Lexington, Ky.). Membranes were then incubated for 45 minutes with a horseradish peroxidase-conjugated secondary antibody (Bio-Rad Laboratories). Enhanced chemiluminescence (Amersham Life Science Inc., Arlington Heights, Ill.) technology was used to detect EGFR signal. Membranes were exposed to Kodak X-OMAR film (Eastman Kodak Co., Rochester, N.Y.) for 15 seconds.

Immunohistochemistry.

Tumor specimens (SCCHN xenografts) were fixed immediately following resection in 10% buffered neutral formalin and stained with hematoxylin-eosin for histopathologic analysis. Indirect immunohistochemical staining for EGFR (Cambridge Research/Genosys Biotechnologies, The Woodlands, Tex.) was performed on paraffin-embedded tissues using a murine monoclonal antibody from a commercially available assay. The labeled streptavidin-biotin (LSAB) method was used to visualize antibody positivity (DAKO LSAB+kits, DAKO Corp., Carpinteria, Calif.). The primary antibody was a mouse antihuman immunoglobulin G (IgG) against the extracellular domain of the receptor (Transduction Labs). The secondary antibody was a horse antimouse biotinylated IgG (Bio-Rad Laboratories). Brown staining was considered positive. Positive and negative controls were as described previously (18). Specimens were interpreted independently by two histopathologists blinded to treatment status of the tumors.

Apoptosis Determinations/DNA Fragmentation.

The percentage of apoptotic cells in tumors treated with the constitutive EGFR antisense (versus sense) U6-based construct was determined by staining for DNA fragmentation (Apotaq). Tumors were harvested, sectioned, fixed in formalin and paraffin embedded, then incubated with proteinase K diluted in phosphate-buffered saline (PBS) for 20 minutes and washed four times in water. Slides were then incubated in 3% $H_2O_2$ in PBS for 5 minutes and washed twice in PBS. Each section was incubated with a terminal transferase enzyme that catalyzes the addition of digoxigenin-labeled nucleotides to the 3'-OH ends of the fragmented DNA for 15 minutes at 37° C. Slides were then placed in stop buffer for 30 minutes at 37° C., followed by washing three times in PBS for 5 minutes. Negative controls are obtained by substituting $dH_2O$ for the terminal deoxynucleotidyl transferase mix. Slides were read and scored under 400× magnifications for the number of positive cells per five high-power fields using computerized image analysis (SAMBA 4000 Image Analysis System; Image Products International, Chantilly, Va.).

Statistical Analysis.

For in vivo experiments in which tumor volumes of the same mice were measured over time, the statistical significance of differences between groups was examined by use of repeated measures analysis of variance (two-sided). Comparisons were restricted to mice in the same experiment. For apoptosis studies, the statistical significance of differences in apoptosis rates was assessed by use of Student's t test (two-sided) that assumed unequal variance.

Results

Modification of U6 Expression Plasmid.

U6 is a small, stable RNA that exists as an abundant small nuclear ribonucleoprotein (U6 snRNP) in all human cells where it plays central roles in both spliceosome assembly and catalysis in nuclear premessenger RNA splicing. Compared with other Pol III-transcribed gene promoters, such as transfer RNA, the U6 promoter has no control regions located within the sequence encoding the structural component of the RNA. Thus, nearly all of the structural U6 core can be replaced with any other sequence without affecting transcript production (19). A modified U6 expression vector, pΔHU6, was generated from the parental plasmid, pGEMmU6[11] 12) by deleting the 5' hairpin loop through PCR-mediated deletion. The deletion was verified by sequence analysis (data not shown). Oligonucleotides (40 bp) targeting the ATG start site of the human EGFR gene was cloned into plasmid pΔHU6 in the sense (pΔHU6-ES) or antisense (pΔHU6-EAS) orientation (FIG. 1).

Antitumor Efficacy of Antisense EGFR/U6 Chimeric Construct.

Figure 2:
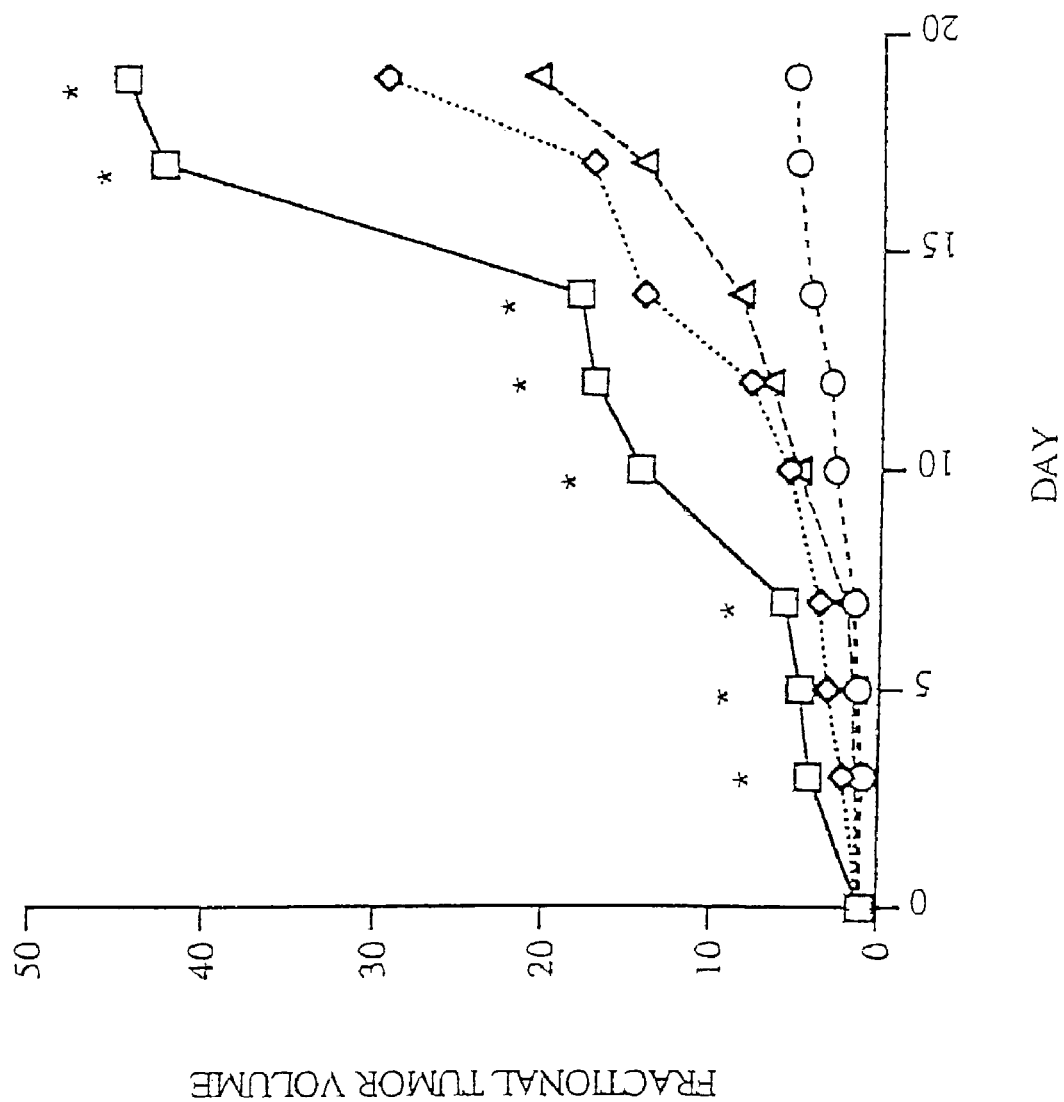
FIG. 2 is a graph showing the in vivo growth inhibition of established squamous cell carcinomas of the head and neck (SCCHN) xenografts. The sustained growth inhibitory effects of the pΔHU6-EAS construct in a representative experiment is demonstrated. Groups of mice received intratumoral treatments (3x/week) with the EGFR antisense construct plus liposomes (○), the antisense construct alone (Δ) the corresponding sense construct with liposomes (◊), or liposomes alone=control (□) 4-21 days following tumor implantation. All cases received eight treatments. Each point represents the mean value for 8 to 10 tumors from an individual experiment that was replicated three times. Fractional tumor volume (tumor volume as a proportion of pretreatment volume) is plotted and the standard error of tumor volumes for all points was less than 10% of the mean. Statistical analysis was performed comparing fractional tumor volumes in the EGFR antisense-treated plus liposome group with the sense-treated group at each time point and significant values (*) were obtained at nearly all time points (two-sided; P<0.05).

To determine whether treatment of established tumors with the EGFR antisense gene expression vector resulted in inhibition of tumor growth, a xenograft model was developed using 1483 cells inoculated subcutaneously in nude mice. DC-Chol cationic liposomes were selected, since they have been shown to be an effective gene transfer vehicle without inducing inflammation in animals (20). Mice were treated three times a week and killed 19 days later when the tumors in the control group(s) had reached 2 cm in maximum diameter. A group of mice was treated with EGFR antisense DNA alone to determine the necessity of the liposomal transfer vehicle. Mice that received the antisense construct plus liposomes were killed at intervals up to 33 days to determine the persistence of the antisense effects. Upon killing the mice, actual tumor volumes and fractional tumor volumes were calculated and at nearly all time points, tumor volumes were significantly lower in the mice that received the EGFR antisense construct (plus liposomes) than in the mice that received the corresponding sense construct (plus liposomes) (FIG. 2). Dose-response studies were also performed and 25 μg of EGFR antisense DNA (plus 25 mmol of DC-Chol liposomes) was found to be as effective as 50 μg/injection in inhibiting tumor growth. A lower dose of 2.5 μg was only modestly effective and 0.25 μg did not abrogate tumor growth (data not shown). There was no difference between actual or fractional tumor volumes in the mice treated with liposomes alone com-pared with the sense construct plus liposomes or the antisense construct alone. Futhermore, the antitumor effect of the antisense therapy was sustained for up to 14 days following cessation of treatment (data not shown). The need for liposomes to mediate gene transfer was verified by the failure to observe growth inhibition in the tumors treated with EGFR antisense DNA alone.

Chimeric U6/EGFR Antisense Gene Expression in SCCHN Cells.

Figure 3A:
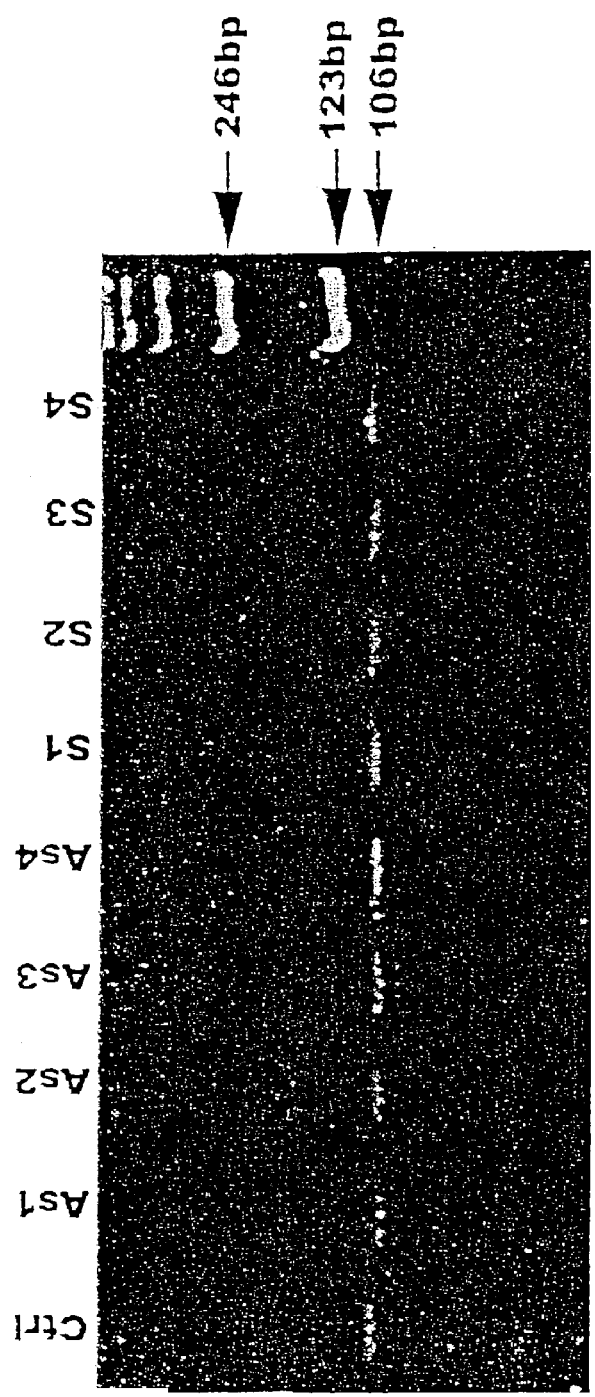
FIGS. 3A and 3B show the expression of chimeric epidermal growth factor receptor (EGFR)/U6 constructs in xenografts from four representative mice treated with intratumoral injections of DNA (sense [S] or antisense [As]) plus liposomes from a single experiment that was replicated three times.
Figure 3B:
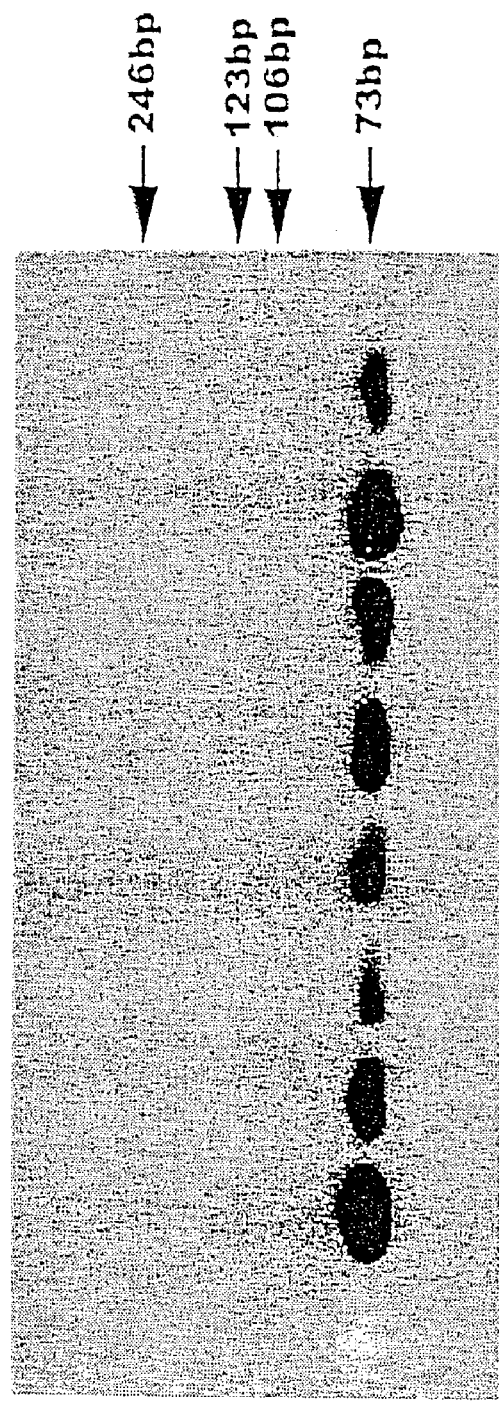

To determine the expression levels of the chimeric antisense (and sense) genes in 1483 cells in vitro, cells were treated with the plasmids pΔHU6-EAS or pΔHU6-ES plus Lipofectamine. The conditions for transfection (e.g., cell density and Lipofectamine concentration) were established for 1483 cells using CMV-LacZ gene delivery and X-gal staining (data not shown). Two days later, total RNA was extracted and primer extension analysis was performed to determine levels of chimeric gene expression (antisense or sense) in transiently transfected cells in vitro. Since the primer used can hybridize to both the endogenous U6 snRNA and the U6/EGFR chimeric RNA, the amount of endogenous U6 snRNA can be used as a normalization control to quantify chimeric gene expression (approximately 0.5 million copies per cell for the endogenous U6 snRNA). The number amount of U6/EGFR chimeric RNA copies per cell was calculated to be $6.3 \times 10^5$ for the EGFR antisense chimeric RNA and $1.6 \times 10^6$ for the corresponding sense chimeric RNA two days after transfection (approximately 0.5 million copies per cell for the endogenous U6 snRNA). The chimeric RNA was easily detected up to 1 week after transfection (data not shown). To determine chimeric gene expression in vivo, tumors treated with the plasmids pΔHU6-EAS or pΔHU6-ES plus DC-Chol liposomes were harvested, RNA was extracted, and RT-PCR was performed followed by hybridization with labeled oligonucleotides to the EGFR chimeric genes (sense or antisense). As shown in FIG. 3, all of the tumors treated with sense or antisense constructs expressed the appropriate chimeric gene in contrast to the tumors treated with liposomes alone. Since residual DNA may contaminate and give false-positive RT-PCR results, we also ran the PCR reaction without adding AMV reverse transcriptase. The result of the PCR amplification was negative on all of the RNA samples treated with RNase-free DNase (data not shown). This indicated that the RNA samples were free of DNA contamination and that the positive signal detected after RT-PCR came from the U6/chimeric RNA.

Suppression of EGFR Gene Expression in Antisense-transfected Cells and Antisense-treated Tumors.

Figure 4:
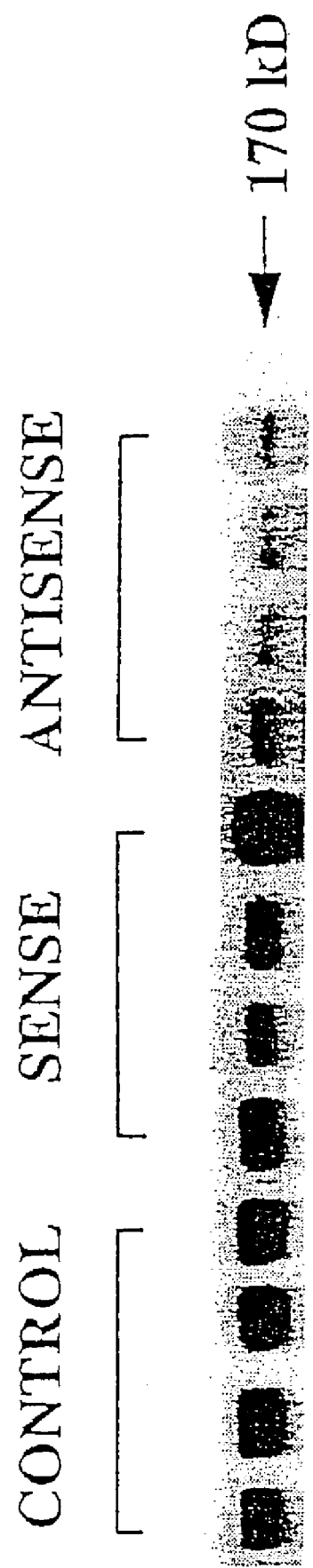
FIG. 4 is an autoradiograph showing suppression of epidermal growth factor receptor (EGFR) protein expression in antisense plus liposome-treated tumors and transiently transfected cells. Panel A shows representative immunoblotting of EGFR protein expression in tumors from mice treated with the EGFR antisense construct (plus liposomes), the EGFR sense construct (plus liposomes), or liposomes alone (control) from an individual experiment that was replicated three times. Crude protein lysates were isolated from each tumor and 50 μg per sample was separated on 10% sodium dodecyl sulfate-polyacrylamide gel electrophoresis that was blotted with mouse-anti-human EGFR monoclonal antibody (Transduction Labs).
Figure 5C:
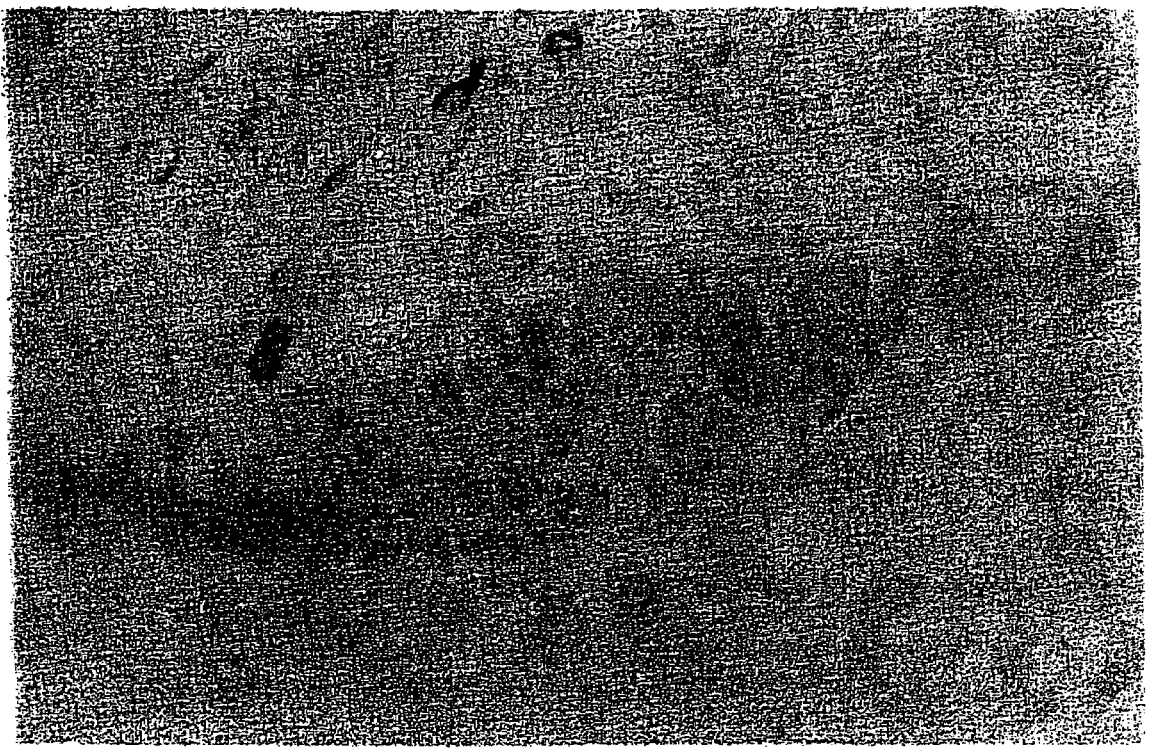
Figure 6:
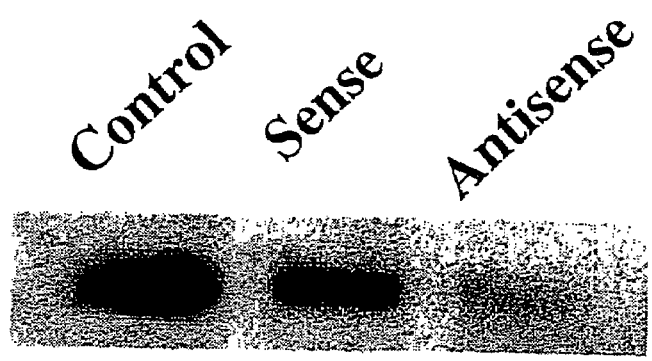
FIG. 6 is an autoradiograph showing the results of epidermal growth factor receptor (EGFR) immunoblotting in 1483 cells transiently transfected with the EGFR antisense (or sense or Lipofectamine alone=control) construct.

To determine that the growth inhibitory effects detected with EGFR antisense treatment were associated with suppression of target (EGFR) gene expression, tumors were harvested and immunoblotting was performed. Treatment with the EGFR antisense expression construct resulted in suppression of EGFR protein expression (FIG. 4). To verify that the suppression in the intact tumor was due to decreased expression in the tumor cells, EGFR immunostaining was performed that demonstrated decreased EGFR staining intensity in the transformed epithelial cells of the antisense-treated tumors (FIGS. 5A-C). Since intact tumors do not represent a pure population of transformed epithelial cells, 1483 cells in vitro were transiently transfected with the EGFR antisense (or sense) construct followed by EGFR immunoblotting. EGFR antisense treatment of these cells in vitro also demonstrated suppression of EGFR protein expression by immunoblotting (FIG. 6).

Increased Apoptosis in Tumors Treated with the Antisense EGFR Construct.

Figure 7:
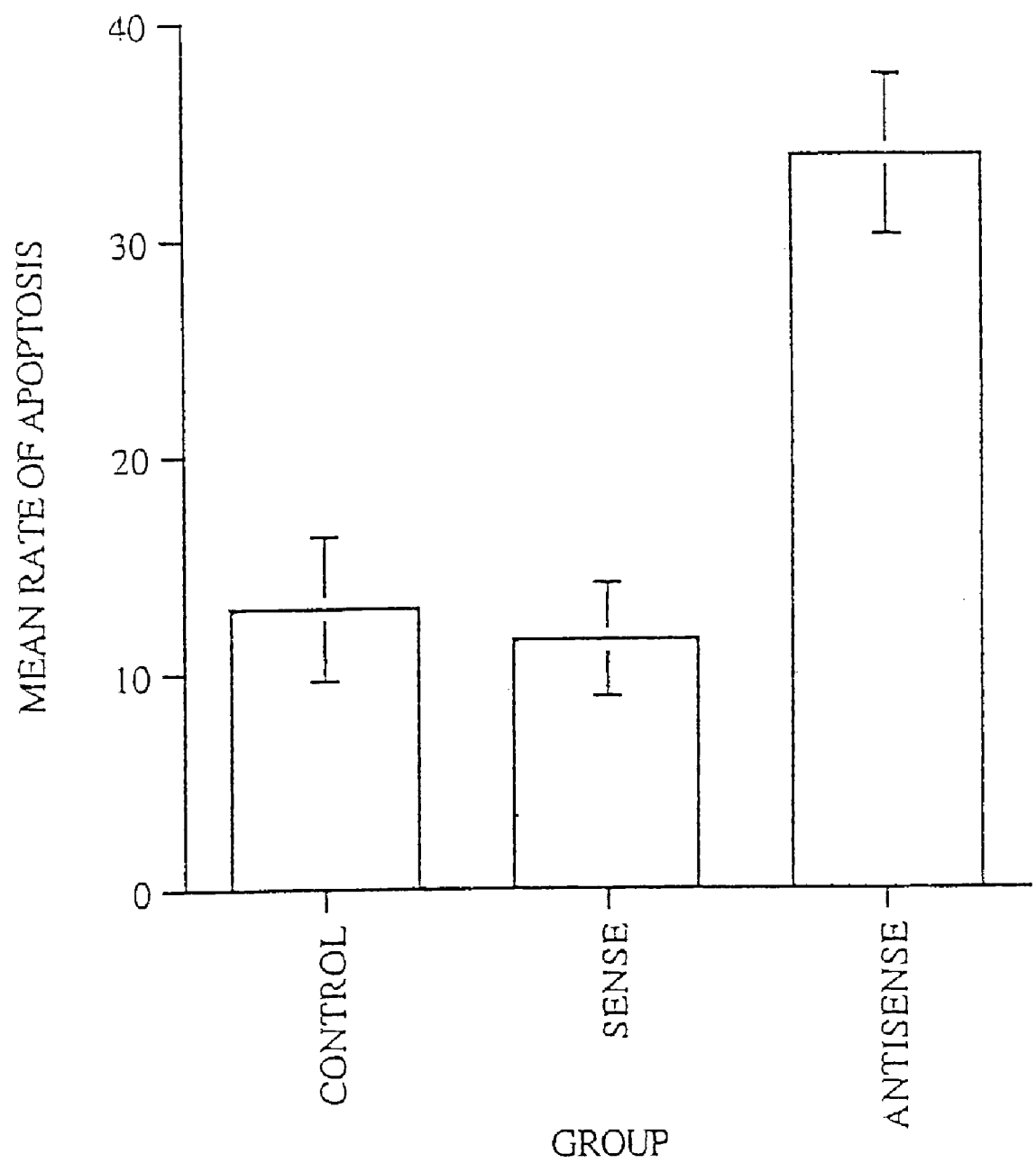
FIG. 7 is a graph showing elevated apoptosis rates in the antisense-treated tumors. Mean rates of apotosis (number of apoptotic cells per five high power fields) in 10 antisense-treated tumors compared with 10 control and 10 sense-treated tumors (two-sided, P=0.007) from an individual experiment that was replicated three times. Bar denotes 95% confidence interval.
Figure 8C:
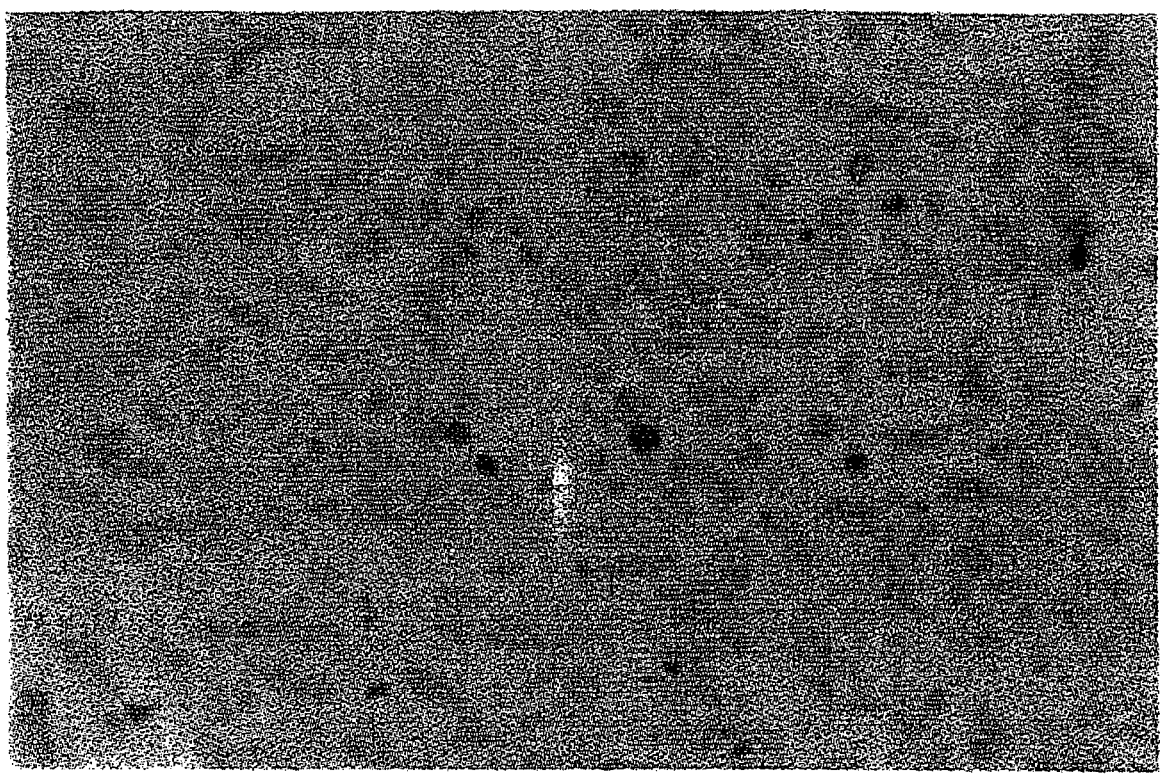

To investigate the mechanism of the antitumor effect induced by treatment with the EGFR antisense construct plus liposomes, we examined hematoxylin-eosin staining of the xenografts and were unable to detect a difference in tumor necrosis between treatment groups (data not shown). To determine whether the observed growth inhibition was associated with an increased rate of programmed cell death, tumors were harvested from each treatment group when the mice were sacraficed (10 mice/group) and stained for DNA fragmentation (Apotaq). Results demonstrated approximately threefold elevation in the rate of apoptosis in tumors treated with the EGFR antisense construct plus liposomes compared with tumors treated with the corresponding sense construct plus liposomes or liposomes alone (two-sided, P=0.007; FIGS. 7 and 8)

The data presented here demonstrate efficient liposomal-mediated transfection of SCCHN cells with an antisense EGFR expression construct under the control of the U6 snRNA promoter in vivo. High expression levels of the chimeric U6 constructs were detected in the tumor cells following treatment of tumor-bearing mice with the EGFR antisense construct plus DC-Chol liposomes, which resulted in sustained growth inhibition, even after the treatments were discontinued. This antitumor effect was accompanied by downregulation of EGFR protein expression in the tumor cells and increased apoptosis. The mechanism of EGFR down-regulation was not specifically addressed.

Epithelial cell transformation has been associated with high expression levels of EGFR and its activating ligand (e.g., TGF-α), which suggests that an autocrine growth pathway may be operating in this tumor system (21,22). It has been demonstrated that SCCHN cells that overexpress EGFR also produce elevated levels of TGF-α (23-26). In such cells, blocking EGFR activation using several strategies, including antisense oligonucleotides, monoclonal antibodies, or EGFR-specific tyrosine kinase inhibitors, resulted in inhibition of SCCHN but not normal epithelial cell proliferation (10). This difference in response to EGFR blocking strategies in normal compared with transformed mucosal squamous epithelial cells may be due to the relatively small number of EGF receptors in normal mucosa. Alternatively, TGF-α/EGFR may be participating in a nonproliferative pathway in normal epithelium as reflected by the primarily suprabasal localization of TGF-α in normal mucosa from patients without cancer in contrast to production by basal, proliferating epithelial cells in normal mucosa harvested several centimeters away from the tumor in patients with SCCHN (18). The failure to inhibit proliferation of normal squamous epithelial cells using EGFR blocking strategies suggests that treatments that target EGFR in SCCHN may result in antitumor effects with minimal toxicity when administered in the region of the carcinoma.

Potential mechanisms of tumor growth inhibition include necrosis and apoptosis. This possibility was investigated by examining the treated tumors for morphologic features of necrosis on hematoxylin-eosin staining. No appreciable difference among the treatment groups was found. However, when the treated tumors were stained for DNA fragmentation, a significantly elevated rate of apoptosis in the tumors treated with the EGFR antisense construct plus liposomes was found as compared to tumors receiving the corresponding sense construct plus liposomes. Elevated apoptosis in transformed epithelial cell lines in vitro following treatment with an anti-EGFR monoclonal antibody has been reported (27).

EGFR overexpression has been implicated as a prognostic indicator in numerous cancers (28). Cancer treatments that target EGFR have been designed to inhibit tumor growth and improve outcome. The construct of the present invention should theoretically be effective for treatment of EGFR-overexpressing tumors where EGFR signaling is associated with a proliferative pathway. Several strategies have been previously employed to inhibit EGFR, including monoclonal antibodies and immunotoxins linked to an EGFR ligand such as TGF-α. Although these therapies have resulted in minimal toxicity, limited antitumor effects have been observed in the clinical setting, most likely due to the requirement for systemic administration and generation of a host immune response (29).

Nonviral vector-mediated gene transfer has several theoretical advantages over virally mediated transfer, including low toxicity, lack of immunogenicity and inflammatory reactions, and the relative ease of obtaining large quantities of vector (20). Cationic liposomes contain a positively charged amine head group linked to a hydrophobic chain. The positively charged group can complex with DNA through the electrostatic charge interaction and the liposome-DNA complex is taken up by the cells through endocytosis. DC-Chol contains a tertiary amine head and a cholesterol linked by a carbamoyl bond (30). It can form a liposome with the helper lipid DOPE. DC-Chol liposomes have been used in several clinical trials with negligible toxicity reported, including the delivery of the allogeneic MHC (major histocompatibility complex) gene into melanoma tumor sites and CFTR (cystic fibrosis transmembrane conductance regulator) gene transfer into nasal epithelia of patients with cystic fibrosis (31,32).

SCCHN tumor sites are relatively accessible to direct inoculation (e.g. oral cavity, oropharynx, hypopharynx, and larynx). The regional cervical lymphatics that comprise the initial (and frequently only) metastatic site are also readily amenable to direct inoculation as demonstrated by other therapeutic approaches that have relied on this route of administration (33,34). Antisense-based gene therapy approaches to cancer rely on the disruption of target gene expression that is thought to be critical for tumor cell proliferation. However, the factors that affect the efficacy of the antisense molecule are largely unknown (35). Variables that might be considered when designing antisense expression vectors include the following: 1) the concentration of the antisense RNA within the cells must be sufficiently high to lead to the hybridization of the antisense RNA to its target; 2) the antisense RNA produced from the expression vector should not contain excessive flanking sequences that might interfere with the accessibility to target RNA; and 3) the length of the antisense RNA should be designed for maximal efficacy. To achieve an optimal antisense strategy, a relatively short (40 bp) antisense oligonucleotides targeting the translation start site of the human EGFR gene was cloned into a modified U6 snRNA construct where we deleted the hairpin loop motif to improve access to target RNA. U6 snRNA expression system offers several theoretical advantages over more commonly used gene transfer vehicles that utilize RNA polymerase II-transcribed promoters (e.g., cytomegalovirus), including 1) U6 snRNA is constitutively expressed in all mammalian cells (0.5 million copies/cell) (36) and the U6 promoter can generate a large amount of short RNA (12); 2) the U6 promoter contains no internal control region thereby allowing replacement of nearly all of the U6 gene with sequence(s) encoding antisense RNA; 3) it now has been determined that only a few nucleotides on the 5' end of U6 RNA are required for the synthesis and stability of U6 chimeric RNA, thus reducing the likelihood of internal folding of the flanking sequence onto the antisense RNA and interference with binding to the target (37); and 4) U6 RNA is retained in the nucleus allowing for targeting of premessenger RNA (11,13). As discussed above, previous studies (38,39) have demonstrated that the first 24 nucleotides in the U6 snRNA that can form a hairpin loop are required for the post-transcriptional modification and thus the stability of the U6 snRNA. However, it has now been found that deletion of this domain does not decrease the amount of chimeric RNA expression in the cell (unpublished data). Since the 5' end hairpin loop could theoretically affect the accessibility of the antisense RNA to the target, this domain was deleted to generate the novel expression vector of the present invention. The results presented herein verify that the U6 expression vector without a 5' hairpin loop is stable and can generate a large amount of U6/chimeric antisense RNA intracellularly.

Pharmaceutically Acceptable Vector.

Figure 11:
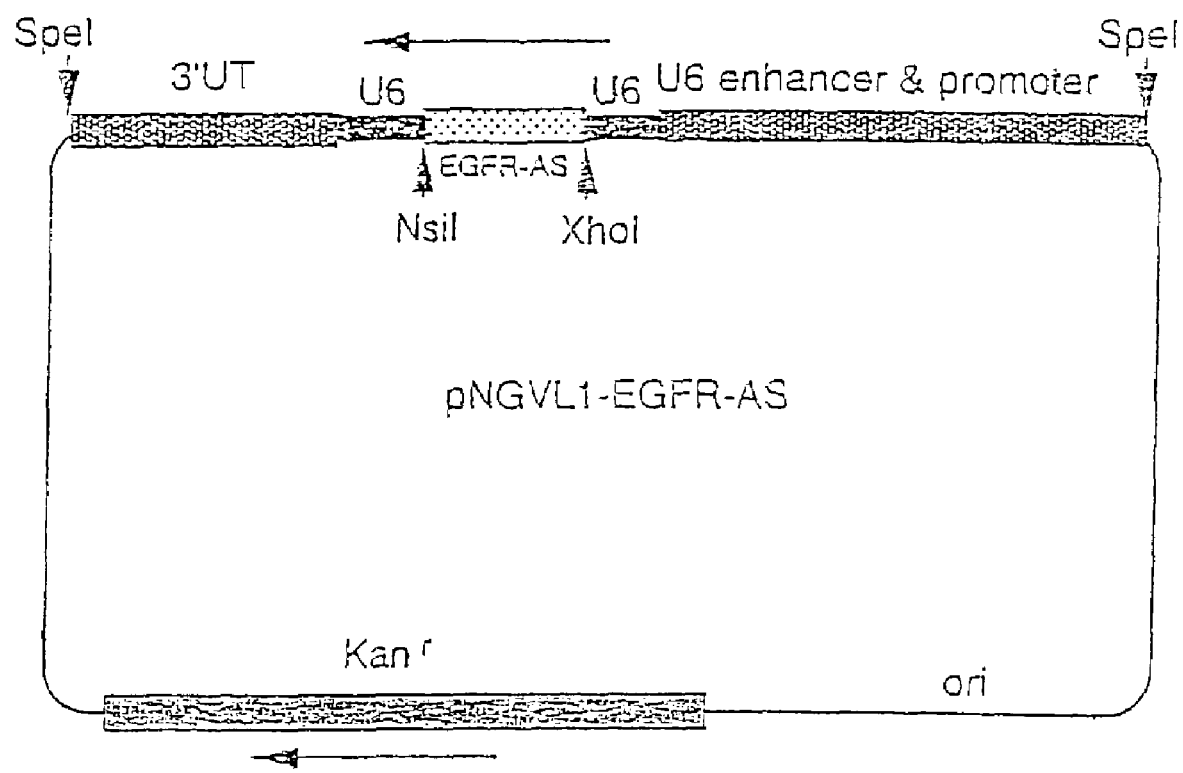

Since plasmid vectors including the Amp$^r$ gene are considered unacceptable for human therapies, a U6/EGFR expression cassette was inserted into a cloning site of a pharmaceutically acceptable plasmid, pNGVL1-EGFR-AS. The sequence of pGVL1 is provided in FIG. 10 (SEQ ID NO: 3) and a plasmid map showing the structure of the antisense EGFR plasmid, pNGVL1-EGFR-AS, is shown in FIG. 11.

The U6 expression cassette was cloned into the SpeI sites of pNGVL1-EGFR-AS, which is 4.0 kb. The sequence from 4 to 88 of the U6 gene was replaced with the EGFR-AS sequence (38nt (SEQ ID NO: 4): 5' CCG GCC GTC CCG GAG GGT CGG ATC GCT GCT CCC CGAAG 3') with Xho I and Nsi I sites at the ends.

Tissue Distribution Studies.

Figure 12:
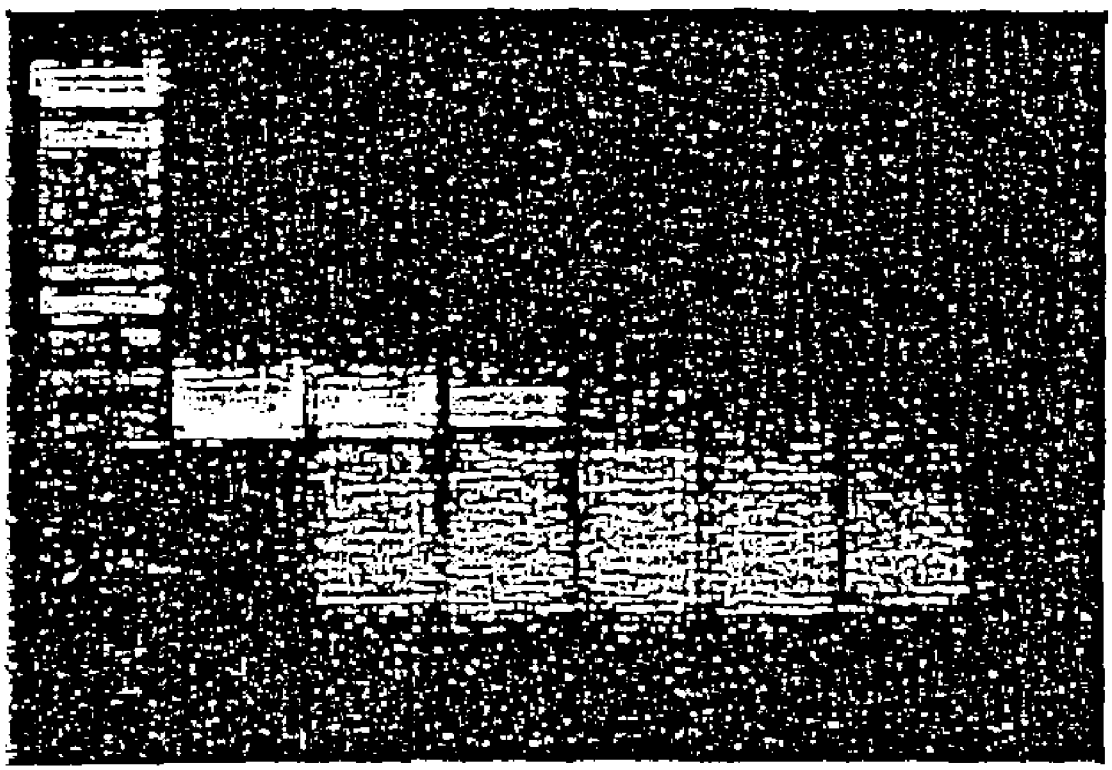
FIG. 12 is a photograph of an ethidium bromide-stained gel showing the sensitivity of the PCR assay for the antisense plasmid DNA. $5 \times 10^{-7}$ μg ($2.07 \times 10^{-4}$ fmol) of EGFR antisense plasmid DNA when mixes with 3 μg RNA extract (from about $1.78 \times 10^5$ cells can be detected. Therefore, it is possible to detect 1.16 fmol plasmid DNA in 1 billion cells by this PCR detection method.

Tissue distribution studies were performed using intramuscular injection of pNGVL1-EGFR-AS (EGFR antisense DNA) plus DC-Chol liposomes into non-tumor bearing, immunocompetent mice (Swiss; 3 males and 3 females at each harvesting time point). The intramuscular route of administration was selected since any injection into a head and neck tumor will likely result in IM administration. A dose of 60 μg (with 60 nmoles of DC-Chol liposomes) was selected by extrapolating preclinical tumor volumes in mice to average human tumor volumes. Using a very sensitive PCR assay that is able to detect 1.16 fmol of antisense DNA in 1 billion cells (see FIG. 12), multiple tissues were examined at 2 days, 7 days and 1 month (plasma, brain, heart, lung, liver, kidney, gonads, injection site (left gastrocnemius muscle), contralateral injection site (right gastrocnemius muscle), draining lymph nodes, and contralateral draining lymph nodes) following a single intramuscular injection of 60 μg of EGFR antisense DNA plus 60 mmoles DC-Chol liposomes.

Figures 13A, 13B:
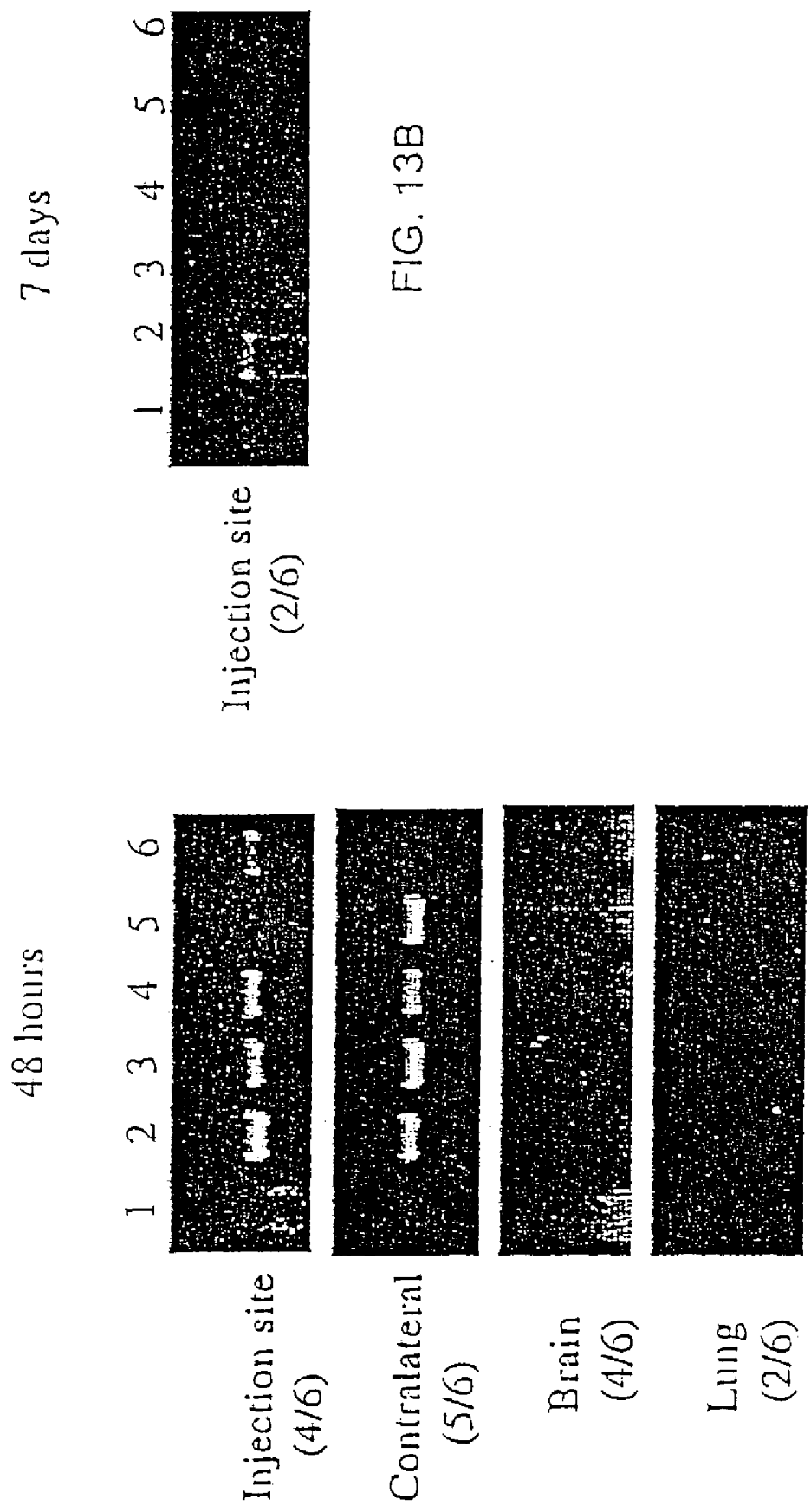
FIGS. 13A and B are photographs of ethidium bromide-stained gels showing the presence of EGFR antisense plasmid DNA in various tissues 48 hours (FIG. 13A) and 7 days (FIG. 13B) after IM injection of the plasmid DNA. After 48 hours after EGFR antisense plasmid DNA injection, this DNA was detected at the injection site (4/6), the contralateral injection site (5/6), the brain (4/6) and the lung (2/6). At 7 days, the DNA was only detected at the injection site and it was undetectable after 1 month.
Figure 14:
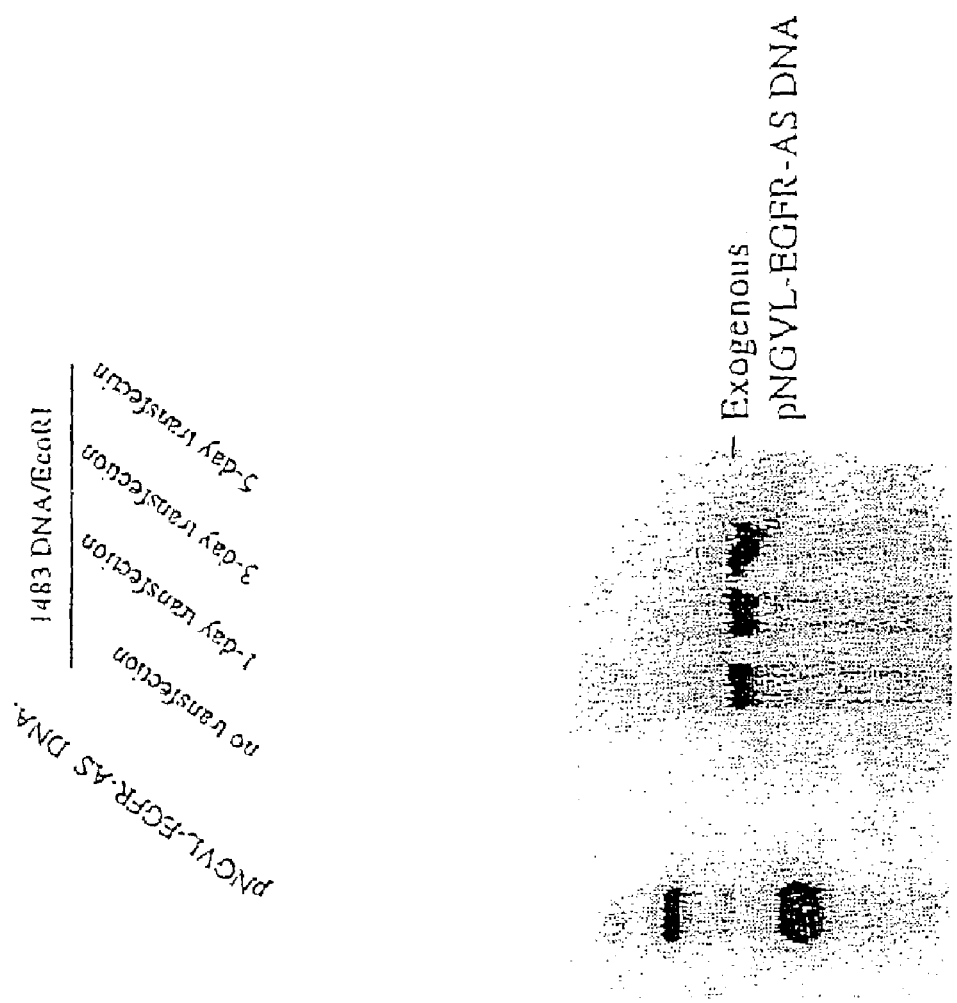
FIG. 14 is an autoradiograph of a Southern blot showing the lack of genomic incorporation of the EGFR antisense plasmid DNA. Only exogenous (non-incorporated) pNGVL-EGFR-AS DNA was detected by this method.

As shown in FIG. 13, at 48 hours, EGFR antisense DNA was detected at the injection site (4/6 mice), the contralateral injection site (5/6 mice), brain (4/6 mice), and the lung (2/6 mice). At 7 days, EGFR antisense DNA was only detected at the injection site (2/6 mice) and EGFR antisense DNA was not detected in any tissues at 1 month following injection. These studies provide the rationale for weekly administration of the pharmaceutical composition of the present invention as a gene therapy. No plasmid DNA is found to be incorporated into the genomic DNA of the host cells by Southern blot analysis (FIG. 14).

The present invention has been described with reference to specific details of particular embodiments thereof. It is not intended that such details be regarded as limitations upon the scope of the invention except insofar as and to the extent that they are included in the accompanying claims.

REFERENCES (1) Salomon D S, Brandt R, Ciardiello R, Nomnanno N. Epidermal growth factor-related peptides and their receptors in human malignancies, Crit. Rev. Oncol. Hematol., 1995; 19:183-232.

(2) Davies D E, Chamberlin S G. Targeting the epidermal growth factor receptor for therapy of carcinomas, Biochem. Pharmacol., 1996; 51:1101-10.

(3) Divigi C R, Welt S, Kris M, Real F X, Yeh S D, Gralla R, et al., Phase I and imaging trial of indium III-labeled anti-epidermal growth factor receptor monoclonal antibody 225 in patients with squamous cell lung carcinoma, J Natl Cancer Inst 1991; 83:97-104.

(4) Baselga J, Norton L, Masui H, Pandielia A, Coplan K, Miller W H Jr., et al. Antitumor effects of doxorubicin in combination with anti-epidermal growth factor receptor monoclonal antibodies, J Natl Cancer Inst 1993; 85:1327-33.

(5) Stragliotto G, Vega F, Stasiecki P, Gropp P, Poisson M, Delattre J Y. Multiple infusions of anti-epidermal growth factor receptor (EGFR) monoclonal antibody (EMD. 55 900) in patients with recurrent malignant gliomas, Eur J Cancer 1996; 32:636-40.

(6) Rusch V, Mendelsohn J, Dmitrovsky E. The epidermal growth factor receptor and its ligands as therapeutic targets in human tumors. Cytokine Growth Factor Rev 1996; 7:133-41.

(7) Phillips P C, Levow C, Catterall M, Colvin O M, Pastan I, Brem H. Transfoming growth factor-alpha-Pseudomonas exotoxin fusion protein (TGF-alpha-PE38) treatment of subcutaneous and intracranial human glioma and medulloblastoma xenografts in athymic mice. Cancer Res 1994; 54:1008-15.

(8) Pastan I, FitzGerald D. Recombinant toxins for cancer treatment. Science 1991; 254:1173-7.

(9) Moroni M C, Willingham M C, Beguinot L. EGF-R antisense RNA blocks expression of the epidermal growth factor receptor and suppresses the transforming phenotype of a human carcinoma cell line. J Biol Chem 1992; 267:2714-22.

(10) Rubin Grandis J, Chakraborty A, Melhem M F, Zeng Q, Tweardy D J. Inhibition of epidermal growth factor receptor gene expression and function decreases proliferation of head and neck squamous carcinoma but not normal mucosal epithelial cells. Oncogene 1997; 15:409-16.

(11) Noonberg S B, Scott G K, Garovoy M R, Benz C C, Hunt C A. In vivo generation of highly abundant sequence-specific oligonucleotides for antisense and triplex gene regulation. Nucleic Acids Res 1994; 22:2830-6.

(12) He Y, Huang L. Growth inhibition of human papillomavirus 16 DNA-positive mouse tumor by antisense RNA transcribed from U6 promoter. Cancer Res 1997; 57:3993-9.

(13) Good P D, Krikos A J, Bertrand E, Lee N S, Giver L, Ellington A, et al. Expression of small, therapeutic RNAs in human cell nuclei. Gene Ther 1997; 4:45-54.

(14) Sacks P G, Parnes S M, Gallick G E, Mansouri Z, Lichtner R, Satya-Prakash K L, et al. Establishment and characterization of two new squamous cell carcinoma cell lines derived from tumors of the head and neck. Cancer Res 1988; 48:2858-66.

(15) Shalinsky D R, Bischoff E D, Gregory M L, Gottardis M M, Hayes J S, Lamph W W, et al. Retinoid-induced suppression of squamous cell differentiation in human oral squamous cell carcinoma xenografts (line 1483) in athymic nude mice. Cancer Res 1995; 55:3183-91.

(16) Sorgi F L, Huang L. Large scale production of DC-Chol cationic liposomes by microfluidization. Into J Pharmaceutics 1996; 144:131-9.

(17) Shamanin V, Delius H, de Villiers E M. Development of a broad spectrum PCR assay for papillomavirus and its application in screening lung cancer biopsies. J Gen Virol 1994; 75(Pt 5):1149-56.

(18) Rubin Grandis J, Melhem M F, Barnes E L, Tweardy D J. Quantitative immunohistochemical analysis of transforming growth factors and epidermal growth factor receptor in patients with squamous cell carcinoma of the head and neck. Cancer 1996; 78:1284-92.

(19) Kunkel G R. RNA polymerase III transcription of genes that lack internal control regions. Biochim Biophys Acta 1991;1088:1-9.

(20) Nabel E G, Gordon D, Yang Z Y, Xu L, San H, Plautz G E. Gene transfer in vivo with DNA-liposome complexes: lack of autoimmunity and gonadal localization. Hum Gen Ther 1992; 3:649-56.

(21) Di Marco E, Pierce J H, Fleming T P, Kraus M H, Molloy C H, Aaronson S A, et al. Autocrine interaction between TGF-α and EGF-receptor: quantitative requirements for induction of the malignant phenotype. Oncogene 1989; 4:831-8.

(22) Ciardiello F, Kim N, Saeki T, Dono R, Persico M G, Plowman G D, et al. Differential expression of epidermal growth factor-related proteins in human colorectal tumors. Proc Natl Acad Sci USA 1991; 88:7792-6.

(23) Rubin Grandis J, Tweardy D J. Elevated levels of transforming growth factor a and epidermal growth factor receptor messenger RNA are early markers of carcinogenesis in head and neck cancer. Cancer Res 1993; 53:3579-84.

(24) Rubin Grandis J, Zeng Q, Tweardy D J. Retinoic acid normalizes the increased gene transcription rate of TGF-α and EGFR in head and neck cancer cell lines. Nat Med 1996; 2:237-40.

(25) Todd R, Donoff B R, Gertz R, Chang A L, Chow P, Matossian K, et al. TGF-α and EGF receptor mRNAs in human oral cancers. Carcinogenesis 1989;10:1553-6.

(26) Christensen M E, Therkildsen M H, Poulsen S S, Bretlau P. Transforming growth factor alpha and epidermal growth factor in laryngeal carcinomas demonstrated by immunohistochemistry. Acta Otolaryngol 1993; 113:563-7.

(27) Wu X, Fan Z, Masui H, Rosen N, Mendelsohn J. Apoptosis induced by anti-epidermal growth factor receptor monoclonal antibody in a human colorectal carcinoma cell line and its delay by insulin. J Clin Invest 1995; 95:1897-905.

(28) Nishikawa R, Ji X D, Harmon R C, Lazar C S, Gill G N, Cavenee W K, et al. A mutant epidermal growth factor receptor common in human glioma confers enhanced tumorigenicity. Proc Natl Acad Sci USA 1994; 91:7727-31.

(29) Snelling L, Miyamoto C T, Bender H, Brady L W, Steplewski Z, Class R, et al. Epidermal growth factor receptor 425 monoclonal antibodies radiolabeled with iodine-125 in the adjuvant treatment of high-grade astrocytomas. Hybridoma 1995; 14:111-4.

(30) Gao X, Huang L. Cationic liposome-mediated gene transfer. Gene Ther 1995; 2:710-22.

(31) Nabel G J, Nabel E G, Yang Z Y, Fox B A, Plautz G E, Gao X, et al. Direct gene transfer with DNA-liposome complexes in melanoma: expression, biological activity, and lack of toxicity in humans. Proc Natl Acad Sci USA 1993; 90:11307-11.

(32) Caplen N J, Alton E W, Middleton P G, Dorin J R, Stevenson B J, Gao X, et al. Liposome-mediated CFTR gene transfer to the nasal epithelium of patients with cystic fibrosis [published erratum appears in Nat Med 1995; 1:272]. Nat Med 1995; 1:39-46.

(33) Vlock D R, Snyderman C H, Johnson J T, Myers E N, Eibling D E, Rubin J S, et al. Phase Ib trial of the effect of peritumoral and intranodal injections of interleukin-2 in patients with advanced squamous cell carcinoma of the head and neck: an Eastern Cooperative Oncology Group Trial. J Immunother Emphasis Tumor Immunol 1994;15:134-9.

(34) Forastiere A A, Urba S G. Single-agent pactitaxel and paclitaxel plus ifosfamide in the treatment of head and neck cancer. Semin Oncol 1995; 22(3 Suppl 6):24-7.

(35) Scherczinger C A, Yates A A, Knecht D A. Variables affecting antisense RNA inhibition of gene expression. Ann N Y Acad Sci 1992; 660:45-56.

(36) Sauterer R A, Feeney R J, Zieve G W. Cytoplasmic assembly of snRNP particles from stored proteins and newly transcribed snRNA's in L929 mouse fibroblasts. Exp Cell Res 1988; 176:344-59.

(37) Kunkel G R, Pederson T. Transcription of a human U6 small nuclear RNA gene in vivo withstands deletion of intragenic sequences but not of an upstream TATATA box. Nucleic Acids Res 1989; 17:7371-9.

(38) Singh R, Gupta S, Reddy R. Capping of mammalian U6 small nuclear RNA in vitro is directed by a conservative stem-loop and AUAUAC sequence: conversion of a noncapped RNA into a capped RNA. Mol Cell Biol 1990; 10:939-46.

(39) Shumyatsky G, Wright D, Reddy R. Methylphosphate cap structure increases the stability of 7SK, B2 and U6 small RNAs in Xenopus oocytes. Nucleic Acids Res 1993; 21:4756-61.

We claim:

1. A pharmaceutical composition for decreasing expression of epidermal growth factor receptor (EGFR) in a cell in vivo, comprising an antisense composition comprising a nucleic acid comprising an expression cassette of plasmid pNGVL1-EGFR-AS deposited under ATCC Accession Number PTA-7774, which includes a human U6 small ribonucleoprotein (snRNP) Polymerase III (Pol III) transcribed gene in which no transcribed portion of the snRNP Pol III-transcribed gene is required for transcription of the gene, the transcribed 5' hairpin structure of the snRNP Pol III-transcribed gene being deleted in which the expression cassette is a U6 expression cassette that includes the human U6 snRNP enhancer, promoter and at least the first 3 nucleotides but no more than about 7 nucleotides and about the last 18 nucleotides of the U6 5' transcribed region operably linked to the antisense EGFR nucleotide sequence, wherein said sequence of an EGFR gene has at least about 20 consecutive nucleotides and said sequence of an EGFR gene is selected from nucleotides 172-209 of SEQ ID NO: 1 and further wherein the composition is a liposome or liposome-forming composition comprising 3β[N-(N',N'-dimethylaminoethane)-carbamoyl] cholesterol.

2. The pharmaceutical composition of claim 1 in which the expression cassette is a U6 expression cassette that includes the human U6 snRNP enhancer, promoter and about 7 nucleotides of the U6 5' transcribed region operably linked to the antisense EGFR nucleotide sequences.

3. The pharmaceutical composition of claim 2 in which the expression cassette further comprises about 18 nucleotides of the 3' end of the human U6 snRNP transcribed region operably linked to the 3' end of the antisense EGFR nucleotide sequences.

4. The pharmaceutical composition of claim 1 in which the transcription control sequences of the expression cassette comprise expression control sequences of the human U6 snRNP gene including the U6 promoter, the U6 enhancer and about the first 7 and last 18 nucleotides of the U6 transcribed region.

5. A nucleic acid comprising an expression cassette of plasmid pNGVL1-EGFR-AS deposited under ATCC Accession Number PTA-7774, which includes a human U6 small ribonucleoprotein (snRNP) Polymerase III (Pol III) transcribed gene in which no transcribed portion of the snRNP Pol III-transcribed gene is required for transcription of the gene in which the expression cassette is a U6 expression cassette that includes the human U6 snRNP enhancer, promoter and at least the first 3 nucleotides but no more than about 7 nucleotides and about the last 18 nucleotides of the U6 5' transcribed region operably linked to the antisense EGFR nucleotide sequence, a transcription control sequence's being operably linked to a sequence of an epidermal growth factor receptor (EGFR) gene of at least about 20 consecutive nucleotides, wherein said EGFR gene is selected from nucleotides 172-209 of SEQ ID NO: 1.

6. The nucleic acid of claim 5 in which the expression cassette includes the human U6 snRNP enhancer, promoter and about 7 nucleotides of the U6 5' transcribed region operably linked to the antisense EGFR nucleotide sequence.

7. The nucleic acid of claim 6 in which the expression cassette further comprises about 18 nucleotides of the 3' end of the human U6 snRNP transcribed region operably linked to the 3' end of the antisense EGFR nucleotide sequence.

8. The nucleic acid of claim 5 in which the transcription control sequences of the expression cassette comprise expression control sequences of the human U6 snRNP gene including the U6 promoter, the U6 enhancer and about the first 7 and last 18 nucleotides of the U6 transcribed region.

9. A nucleic acid comprising the expression cassette of plasmid pNGVL1-EGFR-AS deposited under ATCC Accession Number PTA-7774.

10. A composition for decreasing expression of epidermal growth factor receptor (EGFR) in a cell, comprising an antisense composition comprising a nucleic acid comprising an expression cassette of plasmid pNGVL1-EGFR-AS deposited under ATCC Accession Number PTA-7774, which includes a human U6 small ribonucleoprotein (snRNP) Polymerase III (Pol III) transcribed gene in which no transcribed portion of the snRNP Pol III-transcribed gene is required for transcription of the gene, the transcribed 5' hairpin structure of the snRNP Pol III-transcribed gene being deleted, in which the expression cassette is a U6 expression cassette that includes the human U6 snRNP enhancer, promoter, and about the first 7 and last 18 nucleotides of the U6 5' transcribed region operably linked to the antisense EGFR nucleotide sequence, wherein said sequence of an EGFR gene has at least about 20 consecutive nucleotides and said at least about 20 consecutive nucleotides are selected from nucleotides 172-209 of SEQ ID NO. 1.

* * * * *